US012697475B2

(12) United States Patent
Li et al.

(10) Patent No.: US 12,697,475 B2
(45) Date of Patent: Aug. 4, 2026

(54) MICRONEEDLE PATCH BASE LAYER LAMINATION AND SEPARATION DEVICE, MICRONEEDLE PATCH BASE LAYER LAMINATION DEVICE, AND MICRONEEDLE PATCH DEMOLDING AND SEPARATION DEVICE

(71) Applicants: YOUWE (ZHUHAI) BIOTECHNOLOGY CO., LTD, Zhuhai (CN); ZHUHAI CREWAY PHARMACEUTICAL TECHNOLOGY CO., LTD, Zhuhai (CN)

(72) Inventors: Chengguo Li, Zhuhai (CN); Gang Leng, Zhuhai (CN); Yonghao Ma, Zhuhai (CN); Hong Wang, Zhuhai (CN); Lianhua Chen, Zhuhai (CN)

(73) Assignees: YOUWE (ZHUHAI) BIOTECHNOLOGY CO., LTD, Zhuhai (CN); ZHUHAI CREWAY PHARMACEUTICAL TECHNOLOGY CO., LTD, Zhuhai (CN)

( * ) Notice: Subject to any disclaimer, the term of this patent is extended or adjusted under 35 U.S.C. 154(b) by 81 days.

(21) Appl. No.: 18/866,959

(22) PCT Filed: Feb. 22, 2023

(86) PCT No.: PCT/CN2023/077539
§ 371 (c)(1),
(2) Date: Nov. 18, 2024

(87) PCT Pub. No.: WO2023/241088
PCT Pub. Date: Dec. 21, 2023

(65) Prior Publication Data
US 2025/0312583 A1 Oct. 9, 2025

(30) Foreign Application Priority Data

| Jun. 15, 2022 | (CN) | ......................... 202210677584.0 |
| Jul. 21, 2022 | (CN) | ......................... 202210875544.7 |
| Jul. 29, 2022 | (CN) | ......................... 202210914908.8 |

(51) Int. Cl.
*A61M 37/00* (2006.01)

(52) U.S. Cl.
CPC . *A61M 37/0015* (2013.01); *A61M 2037/0023* (2013.01); *A61M 2037/0053* (2013.01); *A61M 2207/10* (2013.01)

(58) Field of Classification Search
CPC .. A61M 2037/0023; A61M 2037/0046; A61M 2037/0053; A61M 2207/10;
(Continued)

(56) References Cited

U.S. PATENT DOCUMENTS

| 5,167,614 A | * | 12/1992 | Tessmann | ................. A61F 2/92 |
| | | | | 623/1.14 |
| 5,423,851 A | * | 6/1995 | Samuels | ................... A61F 2/07 |
| | | | | 606/198 |

(Continued)

FOREIGN PATENT DOCUMENTS

| CN | 101249938 A | 8/2008 |
| CN | 102064087 A | 5/2011 |

(Continued)

OTHER PUBLICATIONS

U.S. Appl. No. 18/866/959.*
(Continued)

*Primary Examiner* — Sonya M Sengupta
(74) *Attorney, Agent, or Firm* — Scully, Scott, Murphy & Presser, P.C.

(57) ABSTRACT
A microneedle patch base layer lamination and separation device and a control method therefor, a microneedle patch
(Continued)

base layer lamination device and a control method therefor, and a microneedle patch demolding and separation device and a control method therefor are provided. The microneedle patch base layer lamination and separation device includes a rack, a movement control mechanism, a movable seat, and a lamination and separation apparatus. The lamination and separation apparatus is arranged on the movable seat, a carrier is supported on the rack, and the movement control mechanism may control the movable seat and/or the carrier to move in a vertical direction and a horizontal direction; the lamination and separation apparatus includes a rotation control mechanism, a rotary table, an elastic pressing head, and an elastic vacuum suction cup.

21 Claims, 32 Drawing Sheets

(58) Field of Classification Search
CPC ... A61M 37/00; A61M 37/0015; B32B 37/10; B32B 41/00; B29C 33/44; B29C 39/36
See application file for complete search history.

(56) References Cited

U.S. PATENT DOCUMENTS

| | | | | |
|---|---|---|---|---|
| 7,691,077 | B2 * | 4/2010 | Kralick | F16K 99/0028 |
| | | | | 604/9 |
| 2005/0203613 | A1 * | 9/2005 | Arney | A61L 31/14 |
| | | | | 623/1.42 |
| 2007/0179428 | A1 * | 8/2007 | Kralick | F16K 99/0028 |
| | | | | 604/9 |
| 2017/0128708 | A1 | 5/2017 | Ueno | |
| 2023/0285170 | A1 * | 9/2023 | Kralick | A61F 2/848 |
| 2025/0312583 | A1 * | 10/2025 | Li | B29C 39/36 |

FOREIGN PATENT DOCUMENTS

| | | | |
|---|---|---|---|
| CN | 107378285 | A | 11/2017 |
| CN | 109367938 | A | 2/2019 |
| CN | 111524860 | A | 8/2020 |
| CN | 211478032 | U | 9/2020 |
| CN | 112340163 | A | 2/2021 |
| CN | 113427706 | A | 9/2021 |
| CN | 113715218 | A | 11/2021 |
| CN | 214824768 | U | 11/2021 |
| CN | 114084454 | A | 2/2022 |
| CN | 115282114 | A | 11/2022 |
| CN | 218399083 | U | 1/2023 |
| JP | 2017158615 | A | 9/2017 |

OTHER PUBLICATIONS

Translation of abstract of CN102417123.*
Translation of claims of CN102417123.*
Translation of description of CN102417123.*
Translation of drawings of CN102417123.*
Translation of abstract of CN106239902.*
Translation of claims of CN215098402.*
Translation of description of CN215098402.*
The first office action of counterpart CN application No. 202210914908.8 was issued on May 15, 2025.
The second office action of counterpart CN application No. 202210914908.8 was issued on Jul. 9, 2025.

* cited by examiner

Fig. 12
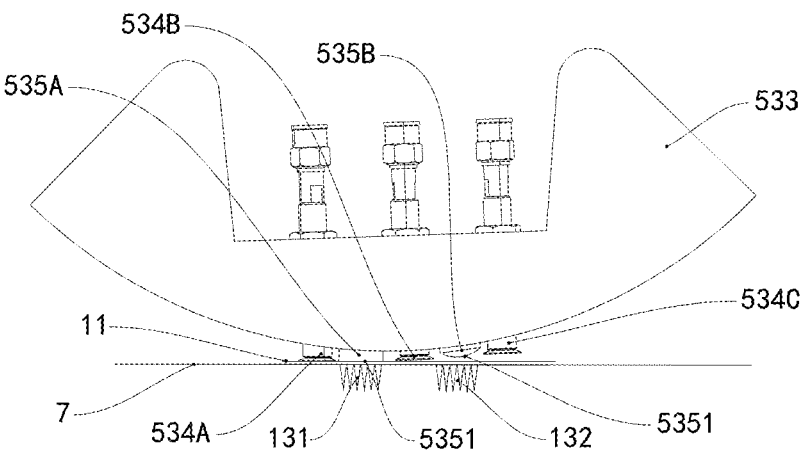
Fig. 13
Fig. 14
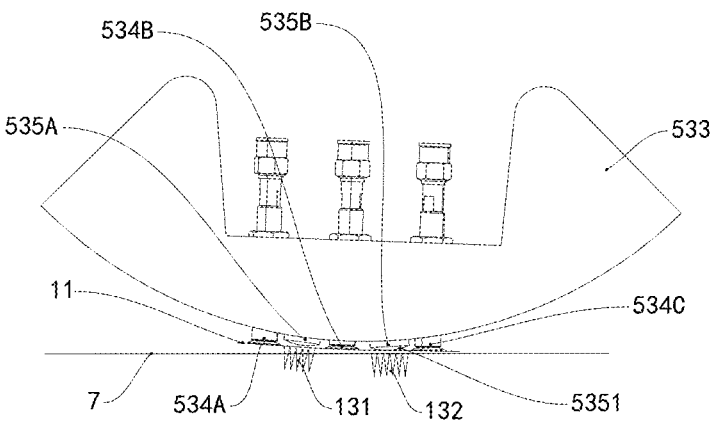

Fig. 22
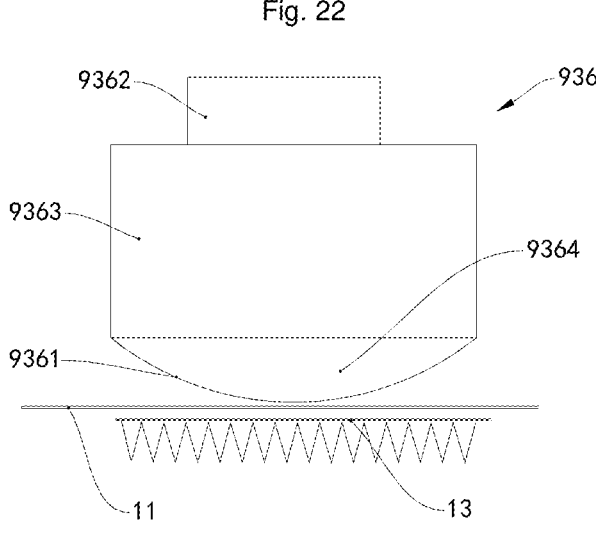
Fig. 23
Fig. 24
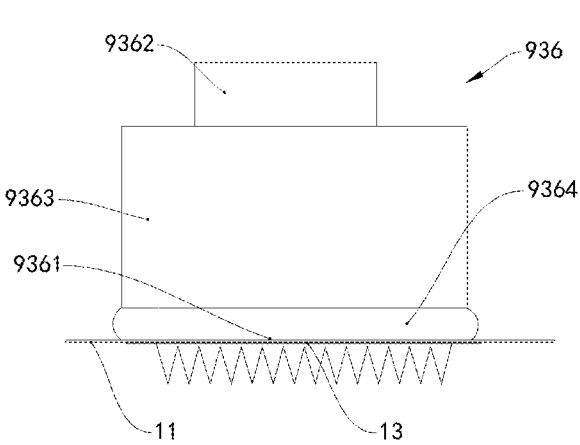

MICRONEEDLE PATCH BASE LAYER LAMINATION AND SEPARATION DEVICE, MICRONEEDLE PATCH BASE LAYER LAMINATION DEVICE, AND MICRONEEDLE PATCH DEMOLDING AND SEPARATION DEVICE

CROSS-REFERENCE TO RELATED APPLICATION(S)

The present disclosure is a national stage application of International Patent Application No. PCT/CN2023/077539, which is filed on Feb. 22, 2023. The International Patent Application claims the priority of Chinese Application No. 202210677584.0, filed in the Chinese Patent Office on Jun. 15, 2022, and entitled "Microneedle Patch Base Layer Lamination and Separation Device and Control Method thereof", the priority of Chinese Application No. 202210875544.7, filed in the Chinese Patent Office on Jul. 21, 2022, and entitled "Microneedle Patch Base Layer Lamination Device and Control Method thereof", the priority of Chinese Application No. 202210914908.8, filed in the Chinese Patent Office on Jul. 29, 2022, and entitled "Microneedle Patch Demolding and Separation Device and Control Method thereof", the entire contents of which are herein incorporated by reference.

TECHNICAL FIELD

The present disclosure relates to the technical field of production devices of microneedle patches for medical and cosmetic purposes, and in particular to a microneedle patch base layer lamination and separation device and a control method therefor, a microneedle patch base layer lamination device and a control method therefor, and a microneedle patch demolding and separation device and a control method therefor.

BACKGROUND

A microneedle patch product is provided with a microneedle array, on which active ingredients such as drugs are provided. The microneedle array may pierce into the skin to form a micro-sized drug delivery channel in the skin in a safe and painless manner, so as to enhance the permeability of the skin to the macromolecular active ingredients and drugs, thereby effectively delivering the active ingredients such as the drugs on the microneedle array into the skin in the safe and painless manner, and achieving transdermal drug delivery.

The microneedle patch is mainly produced by pouring a raw material solution into micro-holes of a mold to form the microneedle array 14 and a base layer 13, and then drying and demolding to form the microneedle patch, that is, the microneedle patch includes the base layer 13 and the microneedle array 14 composed of a plurality of microneedles arranged on the base layer 13, as shown in FIG. 1. After the microneedle patch formed in the mold is dried, cured and formed, the microneedle patch needs to be removed from the mold, that is, a demolding operation is performed. An existing microneedle patch demolding process mainly adopts a vacuum adsorption manner, that is, a vacuum suction cup is adsorbed the base layer 13 of the microneedle patch, and then the vacuum suction cup is controlled to move in a vertical direction, so that the formed microneedle patch is demolded from the mold. Further, as shown in FIG. 1, after the microneedle patch formed in the mold is dried, cured and formed, a support plate 11 adhered with an adhesive layer 12 is placed on the mold. Since the support plate 11 is provided with an accommodating hole 111 corresponding to the microneedle array 14 in a penetrating manner, the support plate 11 is located between the adhesive layer 12 and the base layer 13, a part of the adhesive layer 12 is adhered to a side surface of the support plate 11 away from the base layer 13, the other part of the adhesive layer 12 covers the accommodating hole 111, and then a lamination surface of a pressing head is controlled by a lamination apparatus to laminate the adhesive layer 12 with the base layer 13 of the microneedle patch in the vertical direction, so that the adhesive layer 12 corresponding to the accommodating hole 111 of the support plate 11 is laminated and adhered to the base layer 13 to enable the microneedle patch to be supported by the support plate 11.

Technical Problem

In the process of laminating and separating a base layer of a microneedle patch, a lamination surface of a pressing head of an existing lamination device is a horizontally extended plane. Since an adhesive layer 12 has a flowing characteristic, a surface of the adhesive layer 12 is uneven. When the existing horizontally extended lamination surface performs lamination on the adhesive layer 12 and the base layer 13 of the microneedle patch in a vertical direction, air between the uneven surface of the adhesive layer 12 and the base layer 13 of the microneedle patch is difficult to completely discharge, resulting in obvious bubbles (referring to FIG. 2) between the adhesive layer 12 and the base layer 13 of the microneedle patch. On the one hand, the appearance of a product is affected, and on the other hand, due to the existence of the bubbles, a distance between the microneedle patch and a mold in the separation process is uncontrollable, which easily leads to the breakage of a microneedle or a microneedle tip of the microneedle patch. Consequently, the defective rate of the microneedle patch product is extremely high, thereby greatly increasing the production cost. After the base layer 13 of the microneedle patch is adhered to a support plate 11 through the existing lamination device, the bonded microneedle patch and the support plate 11 need to be separated from a forming female mold of the microneedle patch to obtain a microneedle product, and the existing separation manner adopts a manual operation, that is, the support plate 11 is manually grabbed to drive the microneedle patch to be separated from the forming female mold. Due to the inability to guarantee the skill level of an operator through a manual separation operation, there are problems of unstable process, low production efficiency, high production cost, easiness in damaging the microneedle, and a high reject rate of the product.

In order to solve the above problems existing in the lamination and separation of the base layer of the microneedle patch, a first objective of the present disclosure is to provide a microneedle patch base layer lamination and separation device that integrates a lamination operation and a separation operation, and has a high degree of automation, stable and reliable operation, high yield rate, high production efficiency, and low production cost. A second objective of the present disclosure is to provide a control method for the above microneedle patch base layer lamination and separation device.

In the process of laminating the base layer of the microneedle patch, the lamination surface of the existing pressing head extends in a horizontal direction. Since the adhesive layer 12 has a flowing characteristic, the surface of the adhesive layer 12 is uneven. When the entire lamination surface extending in the horizontal direction is pressed against the adhesive layer 12 to laminate the adhesive layer 12 on the support plate 11 with the base layer 13 of the microneedle patch, the air between the uneven surface of the adhesive layer 12 and the base layer 13 of the microneedle patch is difficult to completely discharge, resulting in obvious bubbles (referring to FIG. 2) between the adhesive layer 12 and the base layer 13 of the microneedle patch. On the one hand, the appearance of the product is affected, and on the other hand, due to the existence of the bubbles, the distance between the microneedle patch and the mold in the separation process is uncontrollable, which easily leads to the breakage of the microneedle or the microneedle tip of the microneedle patch, increases the defective rate of the microneedle patch product, and greatly increases the production cost.

In order to solve the above problems existing in the lamination of the base layer of the microneedle patch, a third objective of the present disclosure is to provide a microneedle patch base layer lamination device with a high degree of automation, stable and reliable operation, high yield rate, high production efficiency, and low production cost. A fourth objective of the present disclosure is to provide a control method for the above microneedle patch base layer lamination device.

In the process of demolding and separating the microneedle patch, a microneedle array 14 is embedded in a micro-hole cavity of the mold, so that the microneedle array 14 has a relatively large adhesion force with the mold, and the base layer 13 of the microneedle patch can better fit the skin and has good flexibility. When a vacuum suction cup moving in the vertical direction is demolded, the vacuum suction cup needs to simultaneously pull all the microneedle arrays 14 out of the micro cavity, and the vacuum suction cup requires a relatively large adsorption force to separate the microneedle patch from the mold. However, the relatively large vacuum adsorption force easily causes the base layer 13 to deform and warp, and even the base layer 13 breaks, resulting in defective products, thereby reducing the yield rate and the production efficiency, and increasing the production cost. When a demolding operation is performed on the microneedle patch supported by the support plate 11, the vacuum suction cup moving in the vertical direction adsorbs the support plate 11 by a relatively large adsorption force. Although the support plate 11 and the adhesive layer 12 support the base layer 13 of the microneedle patch to a certain extent to reduce deformation, there is a weak adhesion between the base layer 13 of the microneedle patch and the adhesive layer 12. When the adsorption force of the vacuum suction cup is greater than the adhesion force between the base layer 13 of the microneedle patch and the adhesive layer 12, the base layer 13 of the microneedle patch is easily separated from the adhesive layer 12 adhered to the support plate 11, and the soft base layer 13 is deformed by the separation and pulling force of the adhesive layer 12, resulting in defective products, thereby reducing the yield rate and the production efficiency, and increasing the production cost. In addition, due to the flexible physical property of the microneedle patch and the sheet physical property of the support plate 11, the existing vacuum suction cup does not have a buffer function when pressing and adsorbing in the vertical direction, which easily presses the base layer 13 of the microneedle patch, the support plate 11, and the adhesive layer 12 into defects such as gravure and embossing, thereby reducing the yield rate.

In order to solve the above problems existing in the demolding and separation of the microneedle patch, a fifth objective of the present disclosure is to provide a microneedle patch demolding and separation device with a high degree of automation, stable and reliable demolding operation, high yield rate, high production efficiency, and low production cost. A sixth objective of the present disclosure is to provide a control method for the above microneedle patch demolding and separation device.

TECHNICAL SOLUTION

In order to achieve a first objective of the present disclosure, the present disclosure provides a microneedle patch base layer lamination and separation device, including a rack, a movement control mechanism, a movable seat, and a lamination and separation apparatus. The lamination and separation apparatus is arranged on the movable seat, a carrier is supported on the rack, and the movement control mechanism is arranged on the rack and is configured to control the movable seat and/or the carrier to move in a vertical direction and a horizontal direction respectively. The lamination and separation apparatus includes a rotation control mechanism, a rotary table, an elastic pressing head, and an elastic vacuum suction cup. The rotary table is able to be located above the carrier in the vertical direction, the rotation control mechanism is configured to control the rotary table to rotate in the horizontal direction, the elastic pressing head and the elastic vacuum suction cup are respectively arranged on a peripheral wall of the rotary table, and an abutting surface, away from the rotary table, of the elastic vacuum suction cup protrudes out of a lamination surface, away from the rotary table, of the elastic pressing head in a radial direction of the rotary table.

In a solution, the lamination surface is arranged as a quadratic surface, and the lamination surface is bent away from the carrier; or, the lamination surface is arranged as a horizontally extended plane, and the lamination surface is tangent to the peripheral wall of the rotary table.

In a further solution, the lamination and separation apparatus further includes at least one mounting base. Each of the at least one mounting base is arranged on the rotary table, and a peripheral wall of the each of the at least one mounting base extends along the peripheral wall of the rotary table, and the peripheral wall of the each of the at least one mounting base is provided with the elastic pressing head and the elastic vacuum suction cup.

In a further solution, the peripheral wall of the each of the at least one mounting base is provided with a plurality of elastic pressing heads and a plurality of elastic vacuum suction cups, the plurality of elastic pressing heads are arranged in a circumferential direction of the rotary table and/or an axial direction of the rotary table, and the plurality of elastic vacuum suction cups are arranged in the circumferential direction of the rotary table and/or the axial direction of the rotary table; and/or, abutting surfaces of the plurality of elastic vacuum suction cups are located on the same plane; and/or, the plurality of elastic pressing heads and the plurality of elastic vacuum suction cups are staggered in a circumferential direction of the rotary table, and/or, the plurality of elastic pressing heads and the plurality of elastic vacuum suction cups are staggered in an axial direction of the rotary table.

In a further solution, the elastic pressing head is made from a combination of Polydimethylsiloxane (PDMS), a curing agent, and a silica sol, and a weight ratio of the PDMS to the curing agent to the silica sol is (12-15):1:(0-3).

In a further solution, the elastic pressing head includes a mounting part, a connecting part, and a lamination part which are connected in sequence, where the lamination surface is located on the lamination part, the peripheral wall of the each of the at least one mounting base is provided with an accommodating groove, and the mounting part is embedded in the accommodating groove; and/or, the elastic pressing head includes a mounting part, a connecting part, and a lamination part which are connected in sequence, where the lamination surface is located on the lamination part, the mounting part and the connecting part are made from the PDMS, the curing agent, and the silica sol in a weight ratio of (12-15):1:(0.5-3), and the lamination part is made from the PDMS, the curing agent, and the silica sol in a weight ratio of (12-15):1:(0-0.5).

In a further solution, a product to be laminated is placed on the carrier, and the product to be laminated includes a microneedle patch, an adhesive layer, and a support plate. The support plate is located between the adhesive layer and a base layer of the microneedle patch, a microneedle array protrudes out of a side, away from the support plate, of the base layer, the support plate is provided with an accommodating hole corresponding to the microneedle array in a penetrating mode, the lamination surface is able to be pressed against a position of the adhesive layer corresponding to the accommodating hole, the abutting surface is able to be pressed against the support plate, a diameter of the peripheral wall of the rotary table is D, a length of the support plate in a rotation direction of the rotary table is L, and D=(4-5)L.

In order to achieve a second objective of the present disclosure, the present disclosure provides a control method for a microneedle patch base layer lamination and separation device. The microneedle patch base layer lamination and separation device is the above microneedle patch base layer lamination and separation device, and the control method includes a lamination step and a separation step. The lamination step includes that: the movement control mechanism controls the movable seat and/or the carrier to move in the vertical direction and the horizontal direction respectively, so that the rotary table is located above a product to be laminated on the carrier in the vertical direction; the movement control mechanism controls the movable seat and/or the carrier to move in the vertical direction, so that a lamination surface of an elastic pressing head can be pressed against an adhesive layer of the product to be laminated; and the rotation control mechanism controls the rotary table to rotate in the horizontal direction, and at the same time, the movement control mechanism controls the movable seat or the carrier to move in the horizontal direction, so that the lamination surface is pressed against the adhesive layer for lamination to form a laminated product. The separation step includes that: the movement control mechanism controls the movable seat and/or the carrier to move in the vertical direction and the horizontal direction respectively, so that the rotary table is located above the laminated product of the carrier in the vertical direction; the movement control mechanism controls the movable seat and/or the carrier to move in the vertical direction, so that an abutting surface of an elastic vacuum suction cup can be pressed against a support plate of the laminated product; and the rotation control mechanism controls the rotary table to rotate in the horizontal direction, and at the same time, the movement control mechanism controls the movable seat or the carrier to move in the horizontal direction, and the elastic vacuum suction cup starts vacuum adsorption, so that the elastic vacuum suction cup adsorbs the support plate to perform a separation operation.

In a further solution, one support plate is provided with a plurality of accommodating holes in a penetrating manner, and after the adhesive layer corresponding to one accommodating hole and the base layer of the product to be laminated complete the lamination step, in the rotation direction of the rotary table, the elastic vacuum suction cup at a front end close to the laminated product completing the lamination step starts vacuum adsorption to perform the separation operation, and at the same time, an elastic pressing head at a rear end close to the laminated product completing the lamination step performs a lamination operation on the adhesive layer corresponding to the next accommodating hole.

In order to achieve a third objective of the present disclosure, some embodiments of the present disclosure provide a microneedle patch base layer lamination device, including a rack, a movement control mechanism, a movable seat, and a lamination apparatus. The lamination apparatus is arranged on the movable seat, a carrier is supported on the rack, and the movement control mechanism is arranged on the rack and is configured to control the movable seat and/or the carrier to move in a vertical direction and a horizontal direction respectively. The lamination apparatus includes a pressure maintaining control mechanism and an elastic pressing head. The elastic pressing head is able to be located above the carrier in the vertical direction, the pressure maintaining control mechanism is used to control the elastic pressing head to move in the vertical direction, a lamination surface, close to the carrier, of the elastic pressing head in the vertical direction is arranged as a quadratic surface, and the lamination surface is bent away from the carrier; or, the lamination surface, close to the carrier, of the elastic pressing head in the vertical direction is inclined relative to the horizontal direction.

In a further solution, a product to be laminated is placed on the carrier, and the product to be laminated includes a microneedle patch, an adhesive layer, and a support plate. The support plate is located between the adhesive layer and a base layer of the microneedle patch, a microneedle array protrudes out of a side, away from the support plate, of the base layer, the support plate is provided with an accommodating hole corresponding to the microneedle array in a penetrating mode, the lamination surface is able to be pressed against a position, corresponding to the accommodating hole, of the adhesive layer, and a projection area of the lamination surface in the horizontal direction is greater than or equal to an adhesion area between the base layer and the adhesive layer.

In a further solution, the lamination surface, close to the carrier, of the elastic pressing head in the vertical direction is inclined relative to the horizontal direction, and an inclination angle between the lamination surface and the horizontal direction is between 1° and 13°.

In a further solution, the lamination surface, close to the carrier, of the elastic pressing head in the vertical direction is arranged as the quadratic surface, the lamination surface is bent away from the carrier, and the lamination surface is arranged as a spherical surface, or, the quadratic lamination surface is arranged as an ellipsoidal surface.

In a further solution, a contact point when the lamination surface is just pressed against the adhesive layer is a contact point A, which is a contact point between the corresponding adhesive layer and the base layer. The maximum arc contact point after the lamination surface is completely laminated with the adhesive layer is a contact point B, an angle between a connecting line between the contact point A and the contact point B and the horizontal direction is θ, and 26°≤θ≤42°.

In a further solution, the elastic pressing head is made from a combination of PDMS, a curing agent, and silica sol, and a weight ratio of the PDMS to the curing agent to the silica sol is (12-15):1:(0-3).

In a further solution, the elastic pressing head includes a mounting part, a connecting part, and a lamination part which are connected in sequence, where the lamination surface is located on the lamination part, and the mounting part and the connecting part are made from the PDMS, the curing agent, and the silica sol in a weight ratio of (12-15): 1:(0.5-3); and/or, the lamination part is made from the PDMS, the curing agent, and the silica sol in a weight ratio of (12-15):1:(0-0.5).

In order to achieve a fourth objective of the present disclosure, some embodiments of the present disclosure provide a control method for a microneedle patch base layer lamination device. The microneedle patch base layer lamination device is the above microneedle patch base layer lamination device, and the control method includes that: the movement control mechanism controls the movable seat and/or the carrier to move in the horizontal direction, so that an elastic pressing head is located above a product to be laminated on the carrier in the vertical direction; the movement control mechanism controls the movable seat and/or the carrier to move in the vertical direction, so that a lamination surface of the elastic pressing head is pressed against an adhesive layer of the product to be laminated; and the pressure maintaining control mechanism controls the elastic pressing head to move downward in the vertical direction, so that the lamination surface is pressed against the adhesive layer and laminated with a base layer of a microneedle patch for lamination to perform a pressure maintaining operation.

In order to achieve a fifth objective of the present disclosure, some embodiments of the present disclosure provide a microneedle patch demolding and separation device, including a rack, a movement control mechanism, a movable seat, and a demolding and separation apparatus. The demolding and separation apparatus is arranged on the movable seat, a carrier is supported on the rack, the movement control mechanism is arranged on the rack and is configured to control the movable seat and/or the carrier to move in a vertical direction and a horizontal direction respectively, the demolding and separation apparatus is able to be located above the carrier in the vertical direction, and the demolding and separation apparatus includes a clamping part and a separation part. The separation part is movably supported on the movable seat in the vertical direction, the separation part protrudes out of the clamping part toward the carrier in the vertical direction, the separation part is configured to force a stripping end of a microneedle patch on the carrier to be demolded, and the clamping part is configured to clamp the stripping end of the microneedle patch.

In a further solution, the separation part is a hook shovel, a hook-off end of the hook shovel is configured to force the stripping end of the microneedle patch to be demolded, and a hook-off surface, connected to the hook-off end, of the hook shovel is configured to support the stripping end of the microneedle patch, and the hook-off surface of the hook shovel extends in an arc shape in the vertical direction, or, the hook-off surface of the hook shovel is inclined relative to the horizontal direction; or, the separation part is a vacuum suction cup, and the vacuum suction cup is able to absorb the stripping end of the microneedle patch to force the stripping end of the microneedle patch to be demolded.

In a further solution, the clamping part includes a first clamping jaw, a second clamping jaw, and a clamping jaw control mechanism. The clamping jaw control mechanism may control the first clamping jaw and the second clamping jaw to move toward or away from each other in the horizontal direction, and the demolding and separation apparatus further includes a clamping control mechanism. The clamping control mechanism is arranged on the movable seat and is used to control the clamping part to move in the vertical direction.

In a further solution, when the separation part is the hook shovel, the clamping part includes a sliding shovel, a pressing block, and a pressing control mechanism. The sliding shovel is located on one side of the hook shovel in the horizontal direction, the pressing block is located above the sliding shovel in the vertical direction, the pressing control mechanism is configured to control the pressing block to move toward or away from the sliding shovel, and the pressing block is able to be pressed against a support surface of the sliding shovel. The support surface of the sliding shovel is configured to support the stripping end of the microneedle patch, the support surface of the sliding shovel is inclined relative to the horizontal direction, and a moving direction of the pressing block is perpendicular to the support surface of the sliding shovel.

In order to achieve a sixth purpose of the present disclosure, some embodiments of the present disclosure provide a control method for a microneedle patch demolding and separation device. The microneedle patch demolding and separation device is the above microneedle patch demolding and separation device, and the control method includes that: the movement control mechanism controls the movable seat and/or the carrier to move in the vertical direction and the horizontal direction respectively, so that a demolding and separation apparatus is located above a mold placed on the carrier in the vertical direction, and the microneedle patch is formed in the mold; the movement control mechanism controls the movable seat and/or the carrier to move in the vertical direction, so that the separation part is pressed against the mold or the microneedle patch; the movement control mechanism controls the movable seat and/or the carrier to move in the horizontal direction or the vertical direction, so that the separation part forces the stripping end of the microneedle patch to be demolded from the mold; the clamping part is controlled to clamp the stripping end of the microneedle patch; and the movement control mechanism controls the movable seat and/or the carrier to move in the vertical direction and the horizontal direction, so that the microneedle patch is demolded from the mold at an angle relative to the horizontal direction.

In a further solution, in a process of demolding the microneedle patch from the mold at an angle relative to the horizontal direction, an inclination angle between the microneedle patch and the horizontal direction is between 43° and 68°.

Beneficial Effect

A microneedle patch base layer lamination and separation device and a control method therefor of the present disclosure integrate a lamination operation and a separation operation, and have a high degree of automation, stable and reliable operation, high yield rate, high production efficiency, and low production cost.

A microneedle patch base layer lamination device and a control method therefor of the present disclosure can effectively and completely discharge bubbles in a laminated product in an inclined direction of a lamination surface, thereby avoiding the possibility of bubbles between an adhesive layer and a base layer of a microneedle patch, ensuring that defective products cannot be caused by the existence of bubbles between the base layer of the microneedle patch and the adhesive layer, and then improving the production yield rate, and have a high degree of automation, stable and reliable operation, high yield rate, high production efficiency, and low production cost.

For a microneedle patch demolding and separation device and a control method therefor of the present disclosure, compared with an existing method that requires a relatively large adsorption force to demold the microneedle patch from a mold in the vertical direction to cause deformation, resulting in defective products, the microneedle patch demolding and separation device of the present disclosure controls the microneedle patch to be smoothly demolded from the mold at an angle relative to the horizontal direction by lifting, which reduces the action force and resistance borne by the microneedle patch in the demolding process, and can effectively avoid the damage and breakage of a microneedle due to deformation of the microneedle patch in the demolding process, thereby improving the yield rate, and the degree of automation is high, and the demolding operation is stable and reliable, thereby improving the production efficiency and reducing the production cost.

BRIEF DESCRIPTION OF THE DRAWINGS

Figure 4:
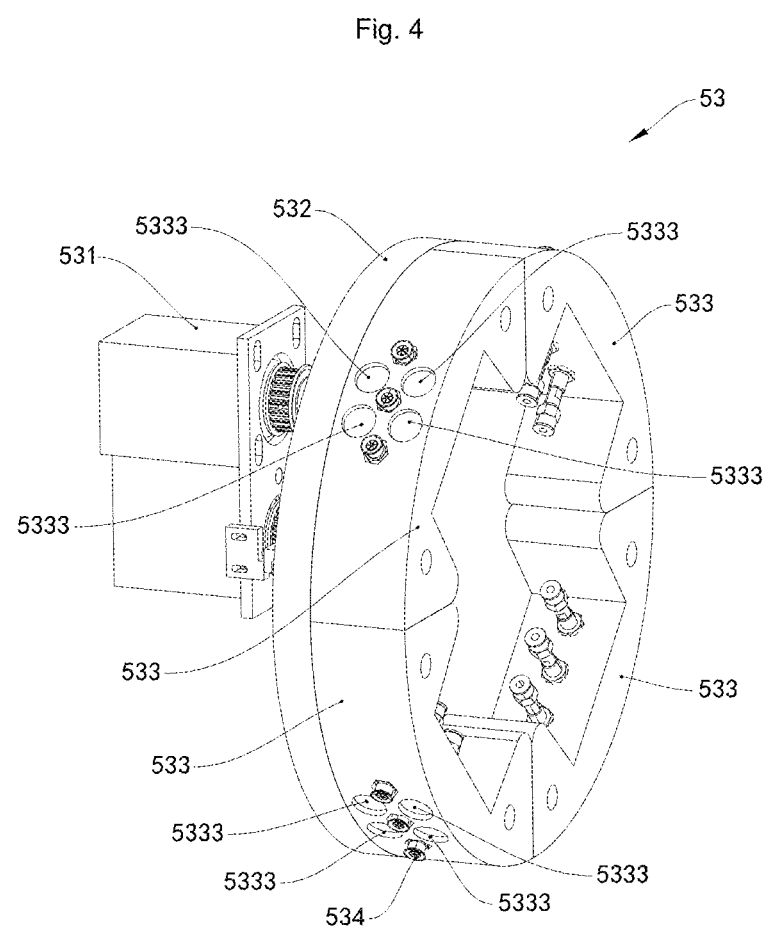

FIG. 4 is a structural diagram of a lamination and separation apparatus in a first embodiment of a microneedle patch base layer lamination and separation device of the present disclosure.

FIG. 12 is a schematic diagram of a second operating state of an elastic pressing head in a first embodiment of a microneedle patch base layer lamination and separation device of the present disclosure during a lamination operation.

FIG. 13 is a schematic diagram of a third operating state of an elastic pressing head in a first embodiment of a microneedle patch base layer lamination and separation device of the present disclosure during a lamination operation.

FIG. 14 is a schematic diagram of a first operating state of an elastic vacuum suction cup in a first embodiment of a microneedle patch base layer lamination and separation device of the present disclosure during a separation operation.

Figures 20, 21:
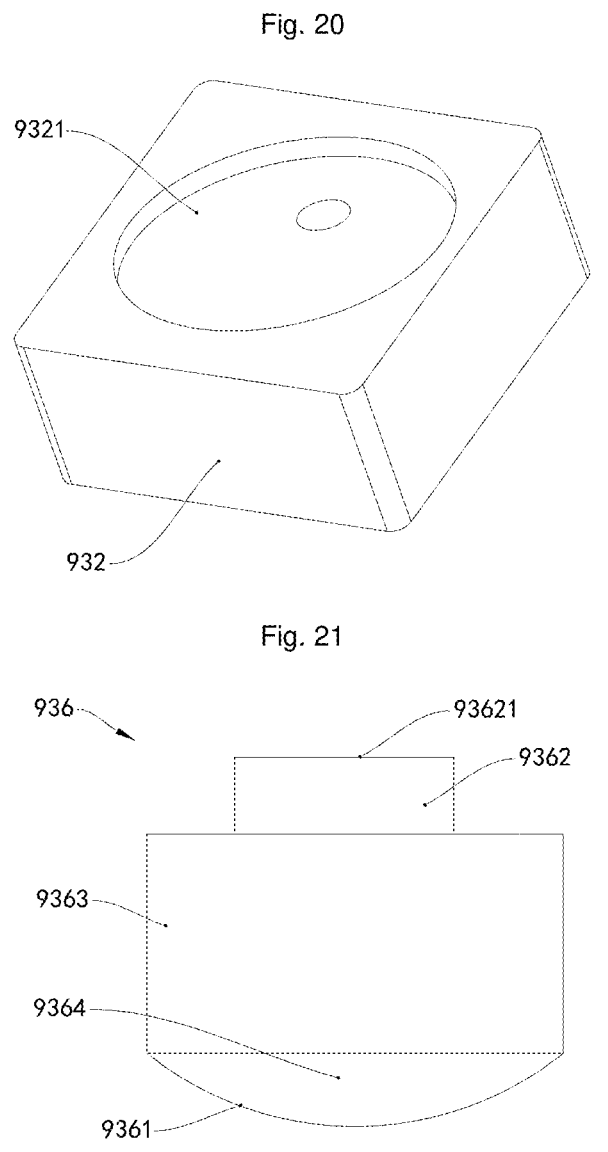

FIG. 20 is a structural diagram of an implementation of a drive seat in a first embodiment of a microneedle patch base layer lamination device of the present disclosure.

FIG. 21 is a front view of a first implementation of an elastic pressing head in a first embodiment of a microneedle patch base layer lamination device of the present disclosure.

FIG. 22 is a front view of a first operating state of a first implementation of an elastic pressing head in a first embodiment of a microneedle patch base layer lamination device of the present disclosure.

FIG. 23 is a front view of a second operating state of a first implementation of an elastic pressing head in a first embodiment of a microneedle patch base layer lamination device of the present disclosure.

FIG. 24 is a front view of a third operating state of a first implementation of an elastic pressing head in a first embodiment of a microneedle patch base layer lamination device of the present disclosure.

Figures 35, 36:
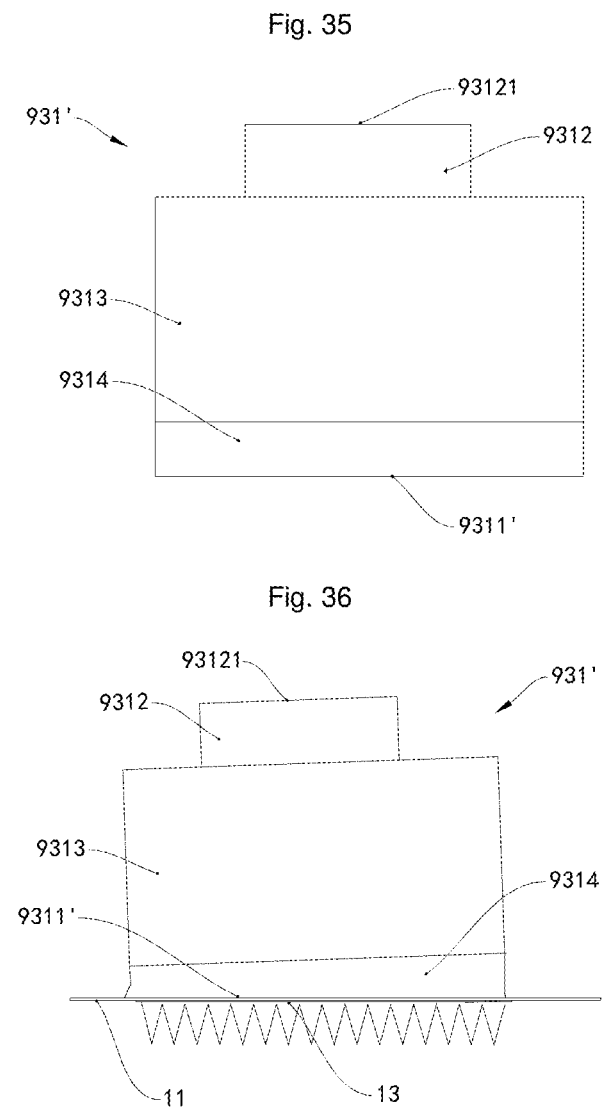

FIG. 35 is a front view of another implementation of an elastic pressing head in a second embodiment of a microneedle patch base layer lamination device of the present disclosure.

FIG. 36 is a front view of an operating state of another implementation of an elastic pressing head in a second embodiment of a microneedle patch base layer lamination device of the present disclosure.

Figure 41:
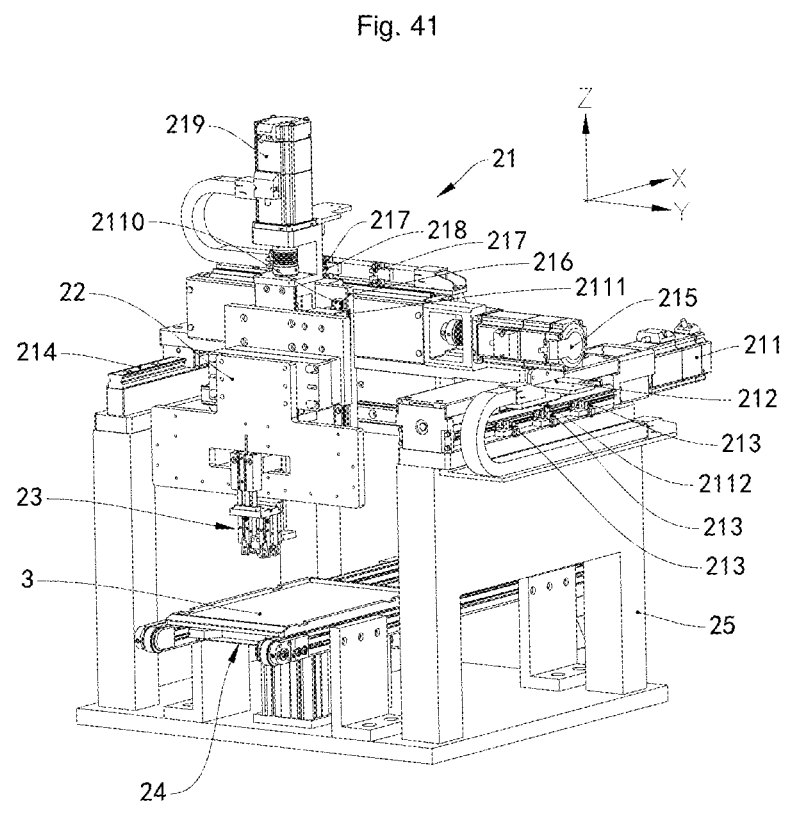

FIG. 41 is a structural diagram of a first embodiment of a microneedle patch demolding and separation device of the present disclosure.

Figure 42:
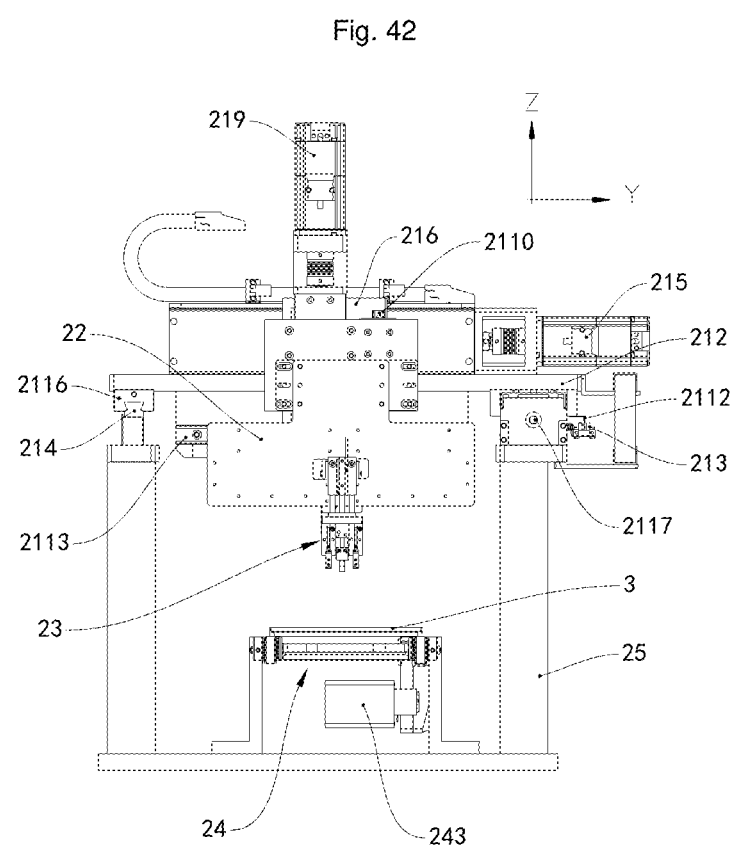

FIG. 42 is a front view of a first embodiment of a microneedle patch demolding and separation device of the present disclosure.

Figure 43:
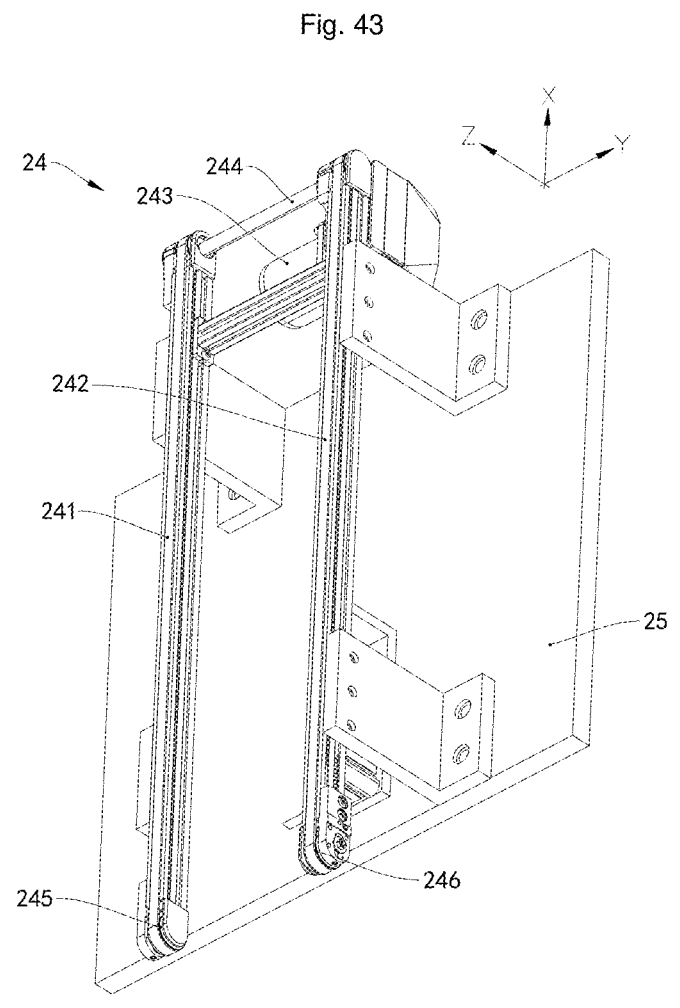

FIG. 43 is a structural diagram of a conveying apparatus in a first embodiment of a microneedle patch demolding and separation device of the present disclosure.

Figure 44:
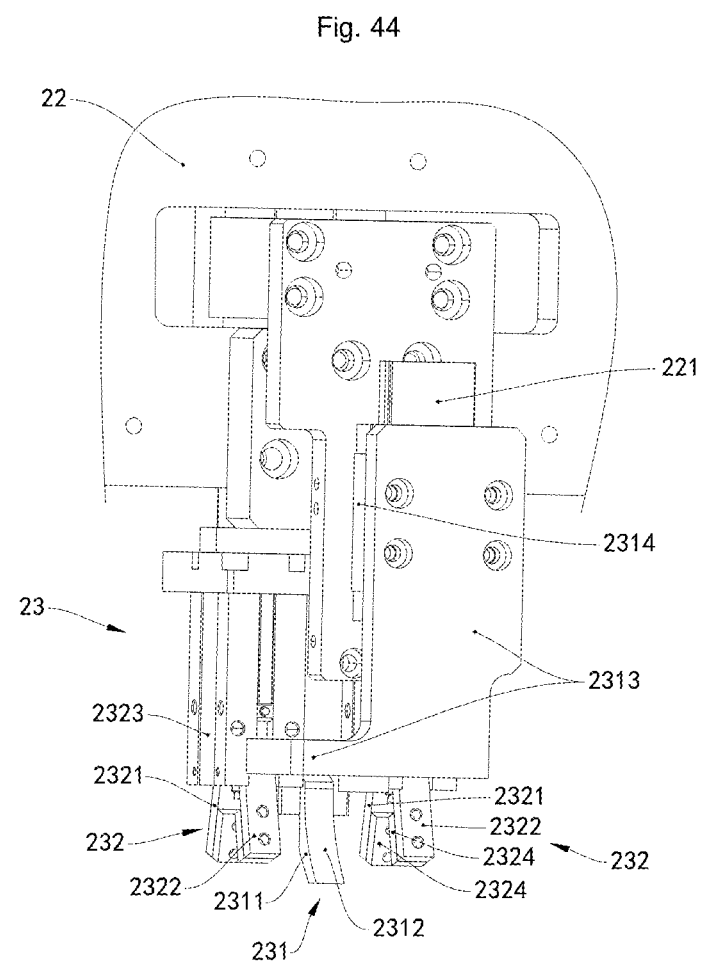

FIG. 44 is a structural diagram of a demolding and separation apparatus in a first embodiment of a microneedle patch demolding and separation device of the present disclosure from a first perspective.

FIG. 48 is a schematic diagram of a second operating state of a first embodiment of a microneedle patch demolding and separation device of the present disclosure.

FIG. 49 is a schematic diagram of a third operating state of a first embodiment of a microneedle patch demolding and separation device of the present disclosure.

FIG. 52 is a schematic diagram of a first operating state of a second embodiment of a microneedle patch demolding and separation device of the present disclosure.

FIG. 53 is a schematic diagram of a second operating state of a second embodiment of a microneedle patch demolding and separation device of the present disclosure.

FIG. 58 is a schematic diagram of a third operating state of a third embodiment of a microneedle patch demolding and separation device of the present disclosure.

The present disclosure is further described below with reference to the accompanying drawings and embodiments.

DETAILED DESCRIPTION OF THE EMBODIMENTS

Figure 1:
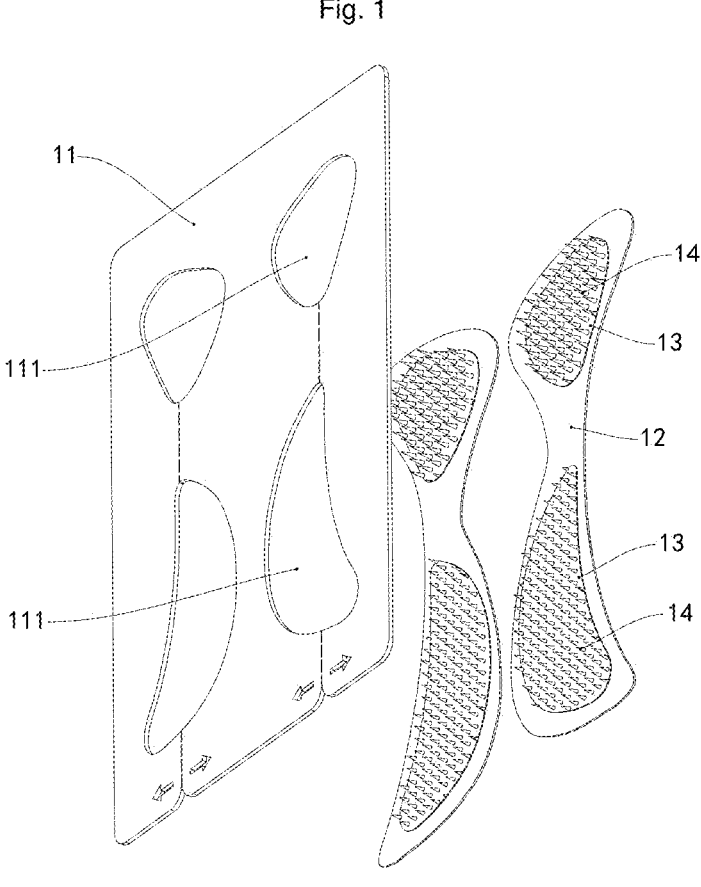
FIG. 1 is an exploded view of a microneedle patch product.
Figure 2:
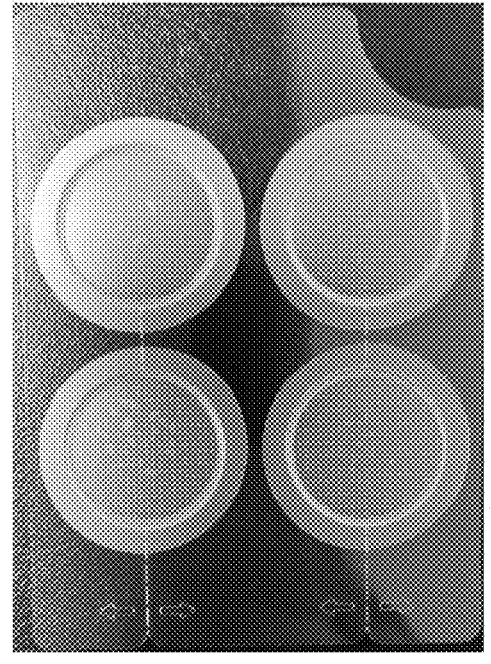
FIG. 2 is a lamination effect diagram of an existing pressing head.
Figure 3:
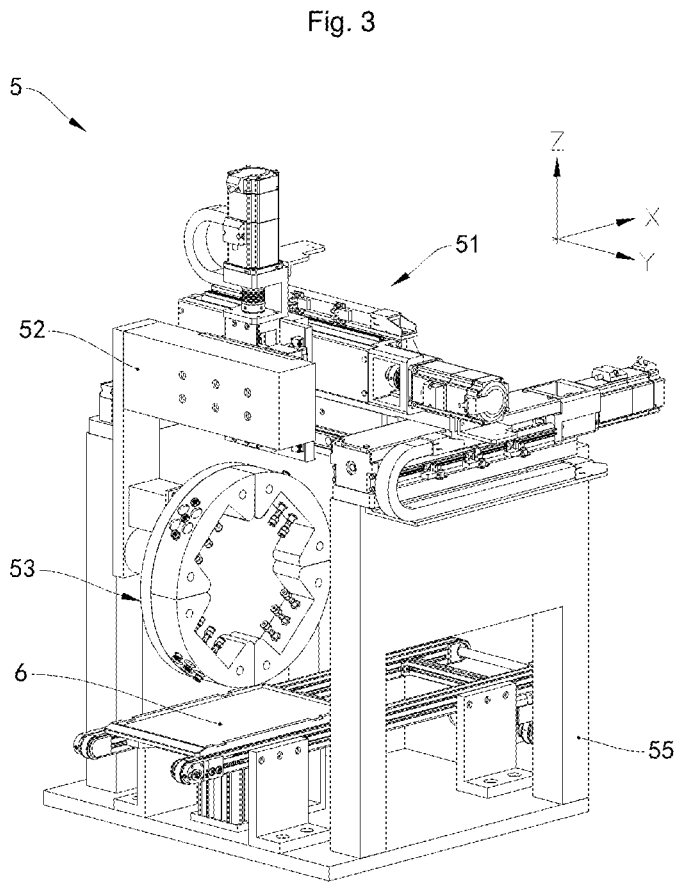
FIG. 3 is a structural diagram of a first embodiment of a microneedle patch base layer lamination and separation device of the present disclosure.
Figure 5:
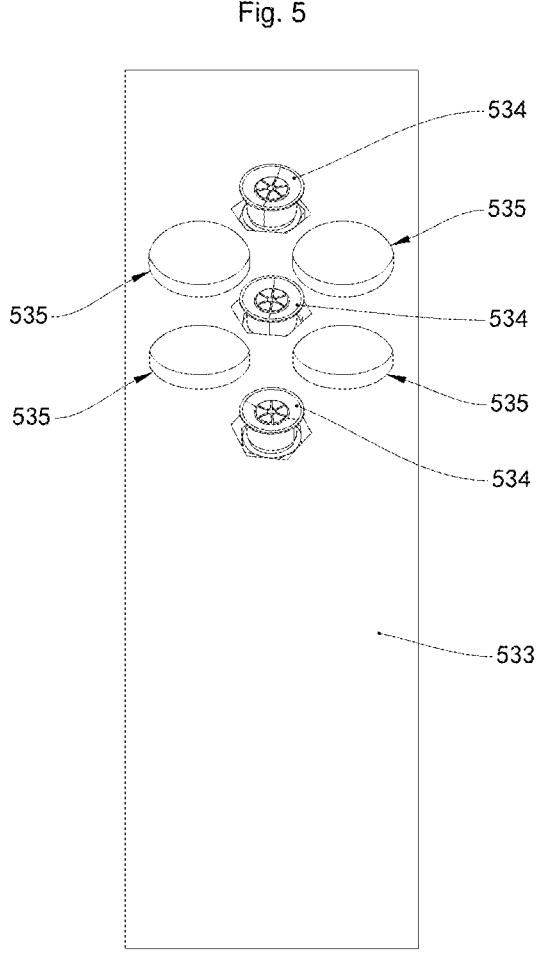
FIG. 5 is a front view of a mounting base in a first embodiment of a microneedle patch base layer lamination and separation device of the present disclosure.
Figures 6, 7:
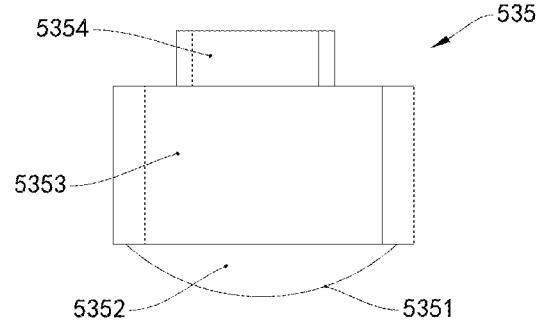
FIG. 6 is a side view of a mounting base in a first embodiment of a microneedle patch base layer lamination and separation device of the present disclosure.
FIG. 7 is a front view of an elastic pressing head in a first embodiment of a microneedle patch base layer lamination and separation device of the present disclosure.
Figure 8:
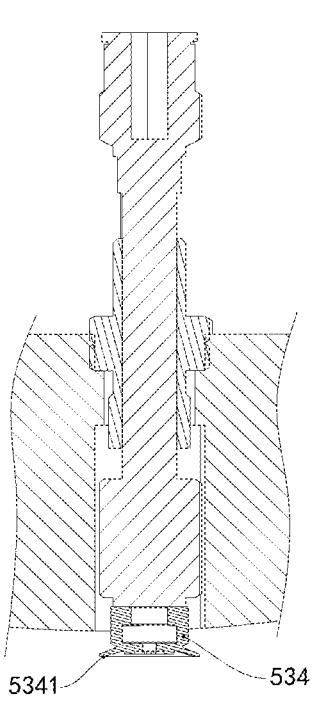
FIG. 8 is a section view of an elastic vacuum suction cup in a first embodiment of a microneedle patch base layer lamination and separation device of the present disclosure.

Referring to FIG. 1, a microneedle patch includes a base layer 13 and a microneedle array 14 composed of a plurality of microneedles arranged on the base layer 13. A support plate 11 is provided with at least one accommodating hole 111 corresponding to the microneedle array 14 in a penetrating manner, and one accommodating hole 111 is configured to accommodate one microneedle array 14 of the microneedle patch. The support plate 11 is located between an adhesive layer 12 and the base layer 13 of the microneedle patch, a part of the adhesive layer 12 is adhered to a side surface, away from the base layer 13, of the support plate 11, the other part of the adhesive layer 12 covers the accommodating hole 111, and one adhesive layer 12 is adapted to one or more accommodating holes 111. The adhesive layer 12 corresponding to the accommodating hole 111 is laminated and adhered to the base layer 13, so that the microneedle patch is supported by the support plate 11.

First embodiment of a microneedle patch base layer lamination and separation device:

Referring to FIG. 3 to FIG. 8, the embodiment discloses a microneedle patch base layer lamination and separation device 5, including a rack 55, a movement control mechanism 51, a movable seat 52, and a lamination and separation apparatus 53. The lamination and separation apparatus 53 is arranged on the movable seat 52, a carrier 6 is supported on the rack 55, the movement control mechanism 51 is arranged on the rack 55 and is able to control the movable seat 52 and/or the carrier 6 to move in a vertical direction and a horizontal direction respectively, and the carrier 6 is configured to place the support plate 11 and a female mold 7 (referring to FIG. 13) filled and cured to form the microneedle patch. The lamination and separation apparatus 53 in the embodiment includes a rotation control mechanism 531, a rotary table 532, an elastic pressing head 535, and an elastic vacuum suction cup 534. The rotary table 532 is able to be located above the carrier 6 in the vertical direction, and the rotation control mechanism 531 is configured to control the rotary table 532 to rotate in the horizontal direction (clockwise/counterclockwise). In addition, the elastic pressing head 535 and the elastic vacuum suction cup 534 in the embodiment are respectively arranged on a peripheral wall of the rotary table 532, an abutting surface 5341, which is away from the rotary table 532, protrudes out of a lamination surface 5351, away from the rotary table 532, of the elastic pressing head 535 in a radial direction of the rotary table 532, the lamination surface 5351 of the elastic pressing head 535 is arranged as a quadratic surface, and the lamination surface 5351 of the elastic pressing head 535 is bent away from the carrier 6. The elastic pressing head 535 is made of an elastic material with uniform performance, so that after the elastic pressing head 535 is elastically deformed, the actual lamination area of the quadratic lamination surface 5351 of the elastic pressing head 535 to a product to be laminated is greater than an adhesion area of the adhesive layer 12 adhered between the base layer 13 of the microneedle patch and the support plate 11. The elastic vacuum suction cup 534 is made of a flexible material, so that the elastic vacuum suction cup 534 has the ability to deform and rebound under force.

The female mold 7 filled with a raw material solution and cured to form the microneedle patch is placed on the carrier 6, and the support plate 11 adhered with the adhesive layer 12 is placed at a corresponding position on the female mold 7, so that the accommodating hole 111 of the support plate 11 matches the position of the base layer 13 of the microneedle patch on the female mold 7, but has a certain distance in the vertical direction, thereby forming the product to be laminated on the carrier 6 of the microneedle patch base layer lamination and separation device 5 in the embodiment.

Figure 9:
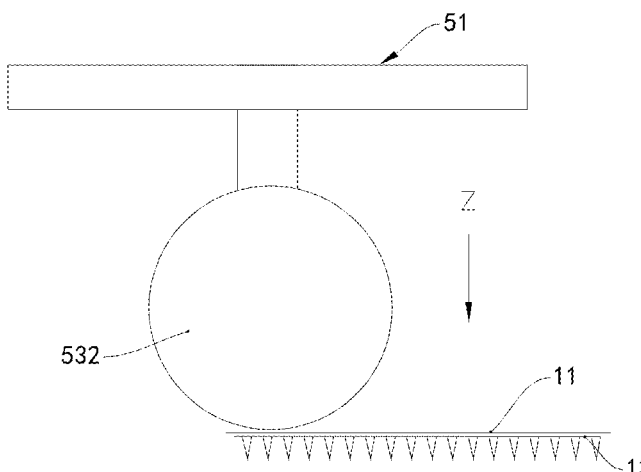
FIG. 9 is a schematic diagram of a first operating state of a first embodiment of a microneedle patch base layer lamination and separation device of the present disclosure.
Figure 10:
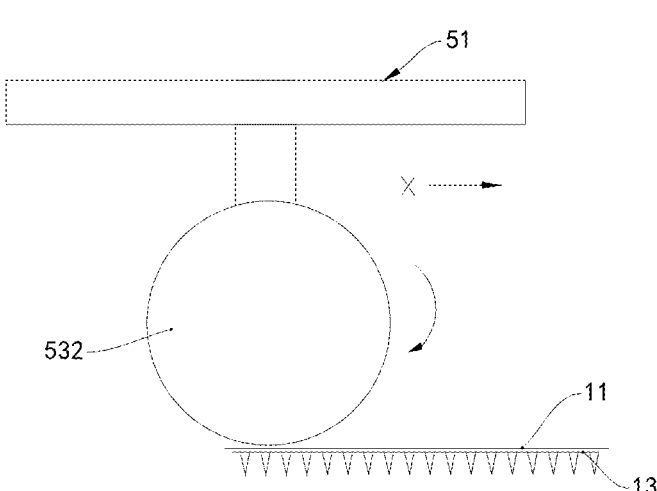
FIG. 10 is a schematic diagram of a second operating state of a first embodiment of a microneedle patch base layer lamination and separation device of the present disclosure.

Referring to FIG. 9 and FIG. 10, in the process of performing a lamination operation or a separation operation, in the embodiment, the movement control mechanism 51 of the microneedle patch base layer lamination and separation device 5 controls the movable seat 52 and/or the carrier 6 to move in the vertical direction and the horizontal direction respectively, so that the rotary table 532 is located above the product to be laminated or the laminated product in the vertical direction, both of which located on the carrier 6. As the movement control mechanism 51 controls the movable seat 52 and/or the carrier 6 to move in the vertical direction (Z-axis direction), the lamination surface 5351 of the elastic pressing head 535 can be pressed against a position, corresponding to the accommodating hole 111 of the support plate 11, of the adhesive layer 12 of the product to be laminated, an abutting surface 5341 of the elastic vacuum suction cup 534 can be pressed against the support plate 11, then the rotation control mechanism 531 controls the rotary table 532 to rotate around the horizontal direction (Y-axis direction), and at the same time, the movement control mechanism 51 controls the movable seat 52 or the carrier 6 to move in the horizontal direction (X-axis direction), so that the lamination surface 5351 of the elastic pressing head 535 is pressed against the position, corresponding to the accommodating hole 111 of the support plate 11, of the adhesive layer 12 to perform the lamination operation, or, the elastic vacuum suction cup 534 starts vacuum adsorption, so that the elastic vacuum suction cup 534 adsorbs the support plate 11 to perform the separation operation.

When the lamination operation or the separation operation is performed, the rotation control mechanism 531 controls the rotary table 532 to rotate around the horizontal direction (Y-axis direction), and at the same time, the movement control mechanism 51 controls the movable seat 52 or the carrier 6 to move in the horizontal direction (X-axis direction), which may effectively avoid defective products caused by the fact that the elastic pressing head 535 and the elastic vacuum suction cup 534 drag the adhesive layer 12 and the support plate 11 to deform in a rotation direction due to the friction between the elastic pressing head 535 and the adhesive layer 12, and between the elastic vacuum suction cup 534 and the support plate 11.

Figure 11:
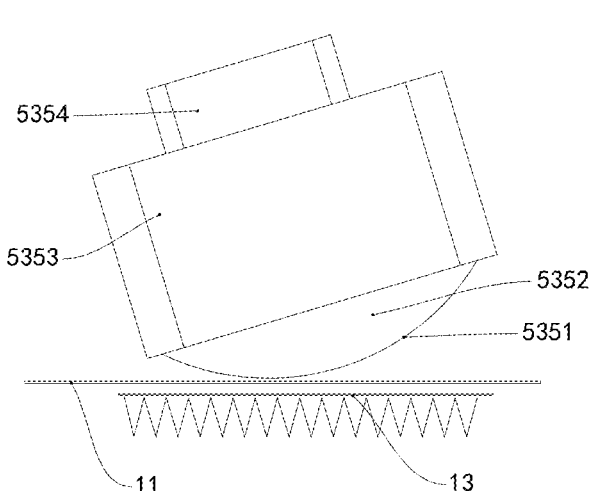
FIG. 11 is a schematic diagram of a first operating state of an elastic pressing head in a first embodiment of a microneedle patch base layer lamination and separation device of the present disclosure during a lamination operation.

Referring to FIG. 11 to FIG. 13, the microneedle patch base layer lamination and separation device 5 in the embodiment performs the lamination operation, as the rotation control mechanism 531 controls the rotary table 532 to rotate around the horizontal direction and the movement control mechanism 51 controls the movable seat 52 or the carrier 6 to move in the horizontal direction, the lamination surface 5351 of the elastic pressing head 535 on the peripheral wall of the rotary table 532 is pressed against the adhesive layer 12 of the product to be laminated on the carrier 6, that is, the lamination surface 5351 of the elastic pressing head 535 is pressed against the position, corresponding to the accommodating hole 111 of the support plate 11, of the adhesive layer 12. As the rotation control mechanism 531 continues controlling the rotary table 532 to rotate round the horizontal direction and the movement control mechanism 51 continues controlling the movable seat 52 or the carrier 6 to move in the horizontal direction, the lamination surface 5351 of the elastic pressing head 535 increases a downward pressure force on the adhesive layer 12 in the vertical direction and performs a pressure maintaining operation, thereby automatically completing the lamination and adhesion between the base layer 13 of the microneedle patch and the adhesive layer 12 to form the laminated product with a high degree of automation. In the process of the lamination operation, since the abutting surface 5341, which is away from the rotary table 532, protrudes outs of the lamination surface 5351 in the radial direction of the rotary table 532, the abutting surface 5341 of the elastic vacuum suction cup 534 can be pressed against the support plate 11 of the product to be laminated to position the support plate 11, so that the lamination operation is stable and reliable. The elastic deformation capability of the elastic vacuum suction cup 534 is greater than that of the elastic pressing head 535 due to the fact that the lamination is not firm or the support plate 11 is damaged when the elastic deformation amount of the elastic vacuum suction cup 534 is less than that of the elastic pressing head 535.

Figure 15:
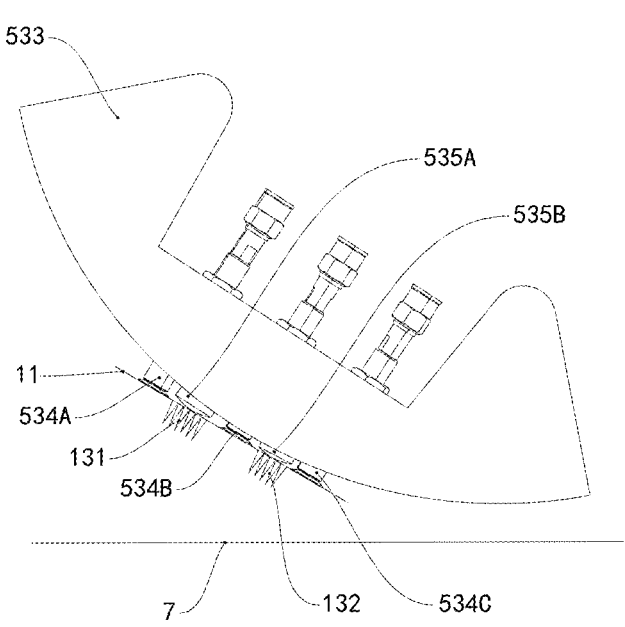
FIG. 15 is a schematic diagram of a second operating state of an elastic vacuum suction cup in a first embodiment of a microneedle patch base layer lamination and separation device of the present disclosure during a separation operation.

Referring to FIG. 14 to FIG. 15, when the microneedle patch base layer lamination and separation device 5 in the embodiment performs the separation operation, as the rotation control mechanism 531 controls the rotary table 532 to rotate around the horizontal direction and the movement control mechanism 51 controls the movable seat 52 or the carrier 6 to move in the horizontal direction, the abutting surface 5341 of the elastic vacuum suction cup 534 on the peripheral wall of the rotary table 532 is pressed against the support plate 11 of the laminated product on the carrier 6, and the elastic vacuum suction cup 534 starts vacuum adsorption, so that the elastic vacuum suction cup 534 is adsorbed on the support plate 11. As the rotation control mechanism 531 continues controlling the rotary table 532 to rotate around the horizontal direction and the movement control mechanism 51 continues controlling the movable seat 52 or the carrier 6 to move in the horizontal direction, the elastic vacuum suction cup 534 adsorbs the support plate 11 to synchronously drive the laminated product to be separated from the female mold 7 on the carrier 6, thereby automatically completing the separation of the laminated product from the female mold 7 to form a microneedle product with a high degree of automation. In the process of performing the separation operation, the abutting surface 5341, which is away from the rotary table 532, protrudes outs of the lamination surface 5351 in the radial direction of the rotary table 532, so as to avoid the lamination surface 5351 of the elastic pressing head 535 from having the excessive external thrust on the adhesive layer 12 of the laminated product and the support plate 11 and affecting the adsorption force of the elastic vacuum suction cup 534 to the support plate 11 of the laminated product, thereby effectively ensuring the operational stability and reliability of the separation operation.

Since the elastic pressing head 535 and the elastic vacuum suction cup 534 in the embodiment both have an elastic deformation capability, when the rotary table 532 drives the elastic pressing head 535 and the elastic vacuum suction cup 534 to rotate around the horizontal direction to perform the lamination operation or the separation operation, the lamination surface 5351 of the elastic pressing head 535 is pressed against the adhesive layer 12 and deformed, and the abutting surface 5341 of the elastic vacuum suction cup 534 is pressed against the support plate 11 and also deformed, so as to avoid rigid collision between the elastic pressing head 535, the elastic vacuum suction cup 534, and the microneedle product, protect the adhesive layer 12, the microneedle patch, and the support plate 11, and further avoid defects such as gravure and embossing on the adhesive layer 12, the microneedle patch, and the support plate 11, thereby improving the yield rate. In some embodiments, the elastic vacuum suction cup 534 has an elastic deformation amount greater than or equal to 3 mm in the radial direction of the rotary table 532, which can ensure that the elastic vacuum suction cup 534 has an excellent elastic deformation capability and effectively avoid rigid collision between the vacuum suction cup and the microneedle product.

The lamination surface 5351, away from the rotary table 532, of the elastic pressing head 535 in the embodiment is arranged as a quadratic surface, and the quadratic surface at least includes a cylindrical surface, an elliptical cylindrical surface, a parabolic cylindrical surface, a spherical surface, an ellipsoidal surface, an elliptical paraboloid, etc. The lamination surface 5351 of the elastic pressing head 535 is bent away from the carrier 6. When the quadratic lamination surface 5351 of the elastic pressing head 535 just abuts against the position, corresponding to the accommodating hole 111 of the support plate 11, of the adhesive layer 12, the quadratic lamination surface 5351 forms a point contact with the product to be laminated, there is still a certain distance between the adhesive layer 12 outside the contact point and the base layer 13 in the vertical direction, and the contact area of the point contact is relatively small, so that the introduction of bubbles at the point contact position can be effectively avoided. As the rotation control mechanism 531 continues controlling the rotary table 532 to rotate around the horizontal direction and the movement control mechanism 51 continues controlling the movable seat 52 or the carrier 6 to move in the horizontal direction, the lamination surface 5351 of the elastic pressing head 535 increases the downward pressure force on the adhesive layer 12 in the vertical direction and performs the pressure maintaining operation, and the lamination area of the quadratic lamination surface 5351 gradually expands from the contact point in the horizontal direction. The actual lamination area of the quadratic lamination surface 5351 after elastic deformation is not less than the adhesion area between the base layer 13 of the microneedle patch and the adhesive layer 12, which can ensure that the quadratic lamination surface 5351 is elastically deformed outward in the horizontal direction from point to surface and is pressed against the product to be laminated, so that bubbles in the laminated product are effectively and completely discharged from the quadratic lamination surface 5351 in the horizontal direction from inside to outside, thereby avoiding the possibility of bubbles forming between the adhesive layer 12 and the base layer 13 of the microneedle patch.

In addition, since the microneedle patch is located on the female mold 7, the microneedle array 14 is located in a microneedle forming groove of the female mold 7, and the base layer 13 of the microneedle patch is supported by the female mold 7. In the embodiment, the female mold 7 is made from a PDMS material, so that the female mold 7 has a certain elastic deformation capability, but the elastic deformation capability of the female mold 7 is less than that of the elastic pressing head 535 and the elastic vacuum suction cup 534. The microneedle array 14 of the microneedle patch is supported by the microneedle forming groove of the female mold 7, which can ensure that the microneedle array 14 of the microneedle patch cannot be damaged by an external force when the elastic pressing head 535 is pressed against the adhesive layer 12 and the elastic vacuum suction cup 534 is pressed against the support plate 11, so as to achieve the integrity of the microneedle patch.

Therefore, the microneedle patch base layer lamination and separation device 5 in the embodiment integrates the lamination operation and the separation operation, and has a high degree of automation, stable and reliable operation, high yield rate, high production efficiency, and low production cost. In order to further improve the operational reliability of the elastic pressing head 535, the lamination surface 5351 of the elastic pressing head 535 in the embodiment is arranged as the spherical surface, or the lamination surface 5351 of the elastic pressing head 535 is arranged as the ellipsoidal surface.

In order to improve the operational reliability and stability of the lamination and separation apparatus 53, the lamination and separation apparatus 53 in the embodiments further includes at least one mounting base 533. The mounting base 533 is arranged on the rotary table 532, and a peripheral wall of the mounting base 533 extends along the peripheral wall of the rotary table 532, and the peripheral wall of the mounting base 533 is provided with the elastic pressing head 535 and the elastic vacuum suction cup 534. In order to further improve the production efficiency of the microneedle patch base layer lamination and separation device 5 in the embodiment, the number of mounting bases 533 in the embodiment is at least two, and the plurality of mounting bases 533 are arranged in a circumferential direction of the rotary table 532, and the peripheral wall of each mounting base 533 is provided with a plurality of elastic pressing heads 535 and a plurality of elastic vacuum suction cups 534. The plurality of elastic pressing heads 535 are arranged in the circumferential direction of the rotary table 532 and/or in an axial direction of the rotary table 532, and the plurality of elastic vacuum suction cups 534 are arranged in the circumferential direction of the rotary table 532 and/or in the axial direction of the rotary table 532. Further, the plurality of elastic pressing heads 535 and the plurality of elastic vacuum suction cups 534 in the embodiment are staggered in the circumferential direction of the rotary table 532, and/or, the plurality of elastic pressing heads 535 and the plurality of elastic vacuum suction cups 534 are staggered in the axial direction of the rotary table 532. In some embodiments, the abutting surfaces 5341 of the plurality of elastic vacuum suction cups 534 on the peripheral wall of the each mounting base 533 are located on the same plane 236, and in the process of performing the separation operation by the plurality of elastic vacuum suction cups 534 on the mounting base 533, since the same support plate 11 is provided with the plurality of accommodating holes 111, the separation operation and the lamination operation are performed synchronously, so as to effectively avoid the separation operation of the laminated microneedle patch from affecting the lamination operation of the microneedle patch to be laminated and causing defective products.

In order to ensure the position uniformity of the mounting bases 533 during replacement, the rotary table 532 in the embodiment is provided with a positioning pin (not shown), the positioning pin extends in the axial direction of the rotary table 532, the mounting base 533 is provided with a positioning hole 2331, the positioning hole 5331 is sleeved on the positioning pin, and the mounting base 533 is fastened to the rotary table 532 through a screw (not shown), that is, the rotary table 532 is provided with a threaded fixing hole (not shown), the mounting base 533 is provided with a countersunk threaded hole 5332, and the screw passes through the countersunk threaded hole 5332 and is in threaded connection with the threaded fixing hole, so as to fasten the mounting base 533 to the rotary table 532.

The elastic pressing head 535 in the embodiment includes a mounting part 5354, a connecting part 5353, and a lamination part 5352 which are connected in sequence. The lamination surface 5351 is located on the lamination part 5352, the peripheral wall of the mounting base 533 is provided with an accommodating groove 5333, and the mounting part 5354 is embedded in the accommodating groove 5333. The elastic pressing head 535 is made of an elastic material, and in the embodiment, the elastic pressing head 535 is preferably made from a combination of Polydimethylsiloxane, a curing agent, and a silica sol, and more preferably, a weight ratio of the Polydimethylsiloxane to the curing agent to the silica sol is (12-15):1:(0-3), more preferably, the mounting part 5354 and the connecting part 5353 of the elastic pressing head 535 are made from the Polydimethylsiloxane, the curing agent, and the silica sol in a weight ratio of (12-15):1:(0.5-3), and the lamination part 5352 of the elastic pressing head 535 is made of the Polydimethylsiloxane, the curing agent, and the silica sol in a weight ratio of (12-15):1:(0-0.5), so that the hardness of the mounting part 5354 and the connecting part 5353 of the prepared elastic pressing head 535 is higher than the hardness of the lamination part 5352 of the elastic pressing head 535. The lamination part 5352 of the elastic pressing head 535 both has good flexibility and a certain rigidity, and the mounting part 5354 and the connecting part 5353 of the elastic pressing head 535 have a relatively large density and relatively high hardness, thereby ensuring that the elastic pressing head 535 cannot deviate due to elastic deformation during the lamination operation. The lamination part 5352 of the elastic pressing head 535 has good flexibility, which can meet the requirement that the actual lamination area of the quadratic lamination surface 5351 located on the lamination part 5352 after elastic deformation is not less than the adhesion area between the base layer 13 of the microneedle patch and the adhesive layer 12. The elastic pressing head 535 can achieve automatic elastic pressure lamination after being deformed by force, and the elastic pressing head 535 can restore the deformation after the external force is released. Moreover, the elastic pressing head 535 has good surface gloss, does not damage the surface of the product, and is good in chemical stability, environmentally friendly and non-toxic, and safe to use.

In order to further improve the operational stability and reliability of the microneedle patch base layer lamination and separation device 5 in the embodiment to ensure the production quality of the product, and further improve the degree of automation, the structure and working principle of the movement control mechanism 51 in the embodiment are the same as those of the movement control mechanism 21 in the first embodiment of the microneedle patch demolding and separation device.

A control method for the microneedle patch base layer lamination and separation device 5 in the embodiment includes a lamination step and a separation step. In the process of reciprocating the lamination step and the separation step, the adhesive layer 12 on the support plate 11 can be laminated with the base layer 13 of the microneedle patch to form the laminated product, and the laminated product can be separated from the female mold 7.

Wherein, the lamination step includes that: the movement control mechanism 51 controls the movable seat 52 and/or the carrier 6 to move in the vertical direction and the horizontal direction respectively, so that the rotary table 532 is located above the product to be laminated in the vertical direction which on the carrier 6; the movement control mechanism 51 controls the movable seat 52 and/or the carrier 6 to move in the vertical direction, so that the lamination surface 5351 of the elastic pressing head 535 can be pressed against the adhesive layer 12 of the product to be laminated; and the rotation control mechanism 531 controls the rotary table 532 to rotate in the horizontal direction, and at the same time, the movement control mechanism 51 controls the movable seat 52 or the carrier 6 to move in the horizontal direction, so that the lamination surface 5351 of the elastic pressing head 535 is pressed against the adhesive layer 12 for lamination to form the laminated product.

The separation step includes that: the movement control mechanism 51 controls the movable seat 52 and/or the carrier 6 to move in the vertical direction and the horizontal direction respectively, so that the rotary table 532 is located above the laminated product of the carrier 6 in the vertical direction; the movement control mechanism 51 controls the movable seat 52 and/or the carrier 6 to move in the vertical direction, so that the abutting surface 5341 of the elastic vacuum suction cup 534 can be pressed against the support plate 11 of the laminated product; and the rotation control mechanism 531 controls the rotary table 532 to rotate in the horizontal direction, and at the same time, the movement control mechanism 51 controls the movable seat 52 or the carrier 6 to move in the horizontal direction, and the elastic vacuum suction cup 534 starts vacuum adsorption, so that the elastic vacuum suction cup 534 adsorbs the support plate 11 to perform the separation operation.

The diameter of the peripheral wall of the rotary table 532 in the embodiment is D, the length of the support plate 11 in a rotation direction of the rotary table 532 is L, and D=(4-5)L. Since the peripheral wall of the mounting base 533 extends along the peripheral wall of the rotary table 532, that is, the diameter of the peripheral wall of the mounting base 533 is D, the length of the support plate 11 in the rotation direction of the mounting base 533 is L, and D=(4-5)L. The plurality of elastic pressing heads 535 and the plurality of elastic vacuum suction cups 534 are mounted on one mounting base 533 to form a set of lamination and separation units. The distribution length of each set of lamination and separation units is less than the length of the support plate 11 in the rotation direction of the mounting base 533.

When D=(4-5)L, the mounting base 533 can complete the separation of the support plate 11 from the female mold 7, that is, the separation operation of the microneedle patch, when rotating by 30°-40°. When D<4L, the rotation angle of the mounting base 533 is too large, the circumferential surface of the mounting base 533 is too curved during rotation, and a lamination angle between the elastic pressing head 535 and the adhesive layer 12 is too large, so that during the lamination operation, gas between the adhesive layer 12 and the base layer 13 of the microneedle patch cannot be completely discharged, a gas residue phenomenon occurs, and bubbles are generated between the adhesive layer 12 and the base layer 13, resulting in defective products. When D>5L, the circumferential surface of the mounting base 533 is too flat during rotation, and the lamination angle between the elastic pressing head 535 and the adhesive layer 12 is too small, so that during the lamination operation, the force acting on the adhesive layer 12 is uneven, the front end is subjected to excessive force, and the rear end is subjected to insufficient force, resulting in that the adhesive layer 12 is not firmly laminated with the base layer 13 of the microneedle patch, casing defective products. In some embodiments, D=(4.3-4.5)L.

The support plate 11 is made of a Polyethylene terephthalate (PET) material, which has a certain toughness and rigidity. When the elastic vacuum suction cup 534 adsorbs the support plate 11 and drives the microneedle patch to be demolded from the female mold 7, deformation is avoided. When one support plate 11 is provided with the plurality of accommodating holes 111 in a penetrating manner, the plurality of microneedle patches may be supported on one support plate 11.

Referring to FIG. 13 to FIG. 15 again, after the lamination surface 5351 of the elastic pressing head 535A is pressed against the adhesive layer 12 corresponding to one accommodating hole 111 of the support plate 11 to enable the adhesive layer 12 and the base layer 13 of the microneedle patch 131 to complete the lamination step, that is, the microneedle patch 131 is supported on the support plate 11 through the adhesion between the base layer 13 and the adhesive layer 12, in the rotation direction of the rotary table 532, the abutting surface 5341 of the elastic vacuum suction cup 534A at the front end close to the laminated product is still pressed against the support plate 11, while the laminated product completing the lamination step, and then the elastic vacuum suction cup 534A at the front end starts vacuum absorption to perform the separation operation. At this time, the elastic vacuum suction cup 534B and the elastic vacuum suction cup 534C do not start vacuum, the elastic pressing head 535B at the rear end close to the laminated product completing the lamination step performs the lamination operation on the adhesive layer 12 corresponding to the next accommodating hole 111, and then the lamination surface 5351 of the elastic pressing head 535B at the rear end is pressed against the adhesive layer 12 corresponding to the next accommodating hole 111 of the support plate 11 to laminate the adhesive layer 12 with the base layer 13 of the next microneedle patch 132, so that the microneedle patch base layer lamination and separation device 5 in the embodiment can perform the lamination and separation steps simultaneously, and the production is efficient. The lamination surface 5351 of the elastic pressing head 535B at the rear end is pressed against the adhesive layer 12 corresponding to the next accommodating hole 111 of the support plate 11, so that after the adhesive layer 12 and the base layer 13 of the microneedle patch 132 complete the lamination step, the elastic vacuum suction cup 534B starts vacuum adsorption to perform the separation operation. When the microneedle patch 132 completes the separation operation, the elastic vacuum suction cup 534C starts vacuum adsorption, so that the laminated product is delivered to the next process under the combined effect of the elastic vacuum suction cups 534A, 534B and 534C, and the microneedle patch base layer lamination and separation device 5 in the embodiment may perform the lamination operation and the separation operation on the product to be laminated simultaneously, thereby improving the production efficiency.

Specifically, in the rotation direction of the mounting base 533, the elastic vacuum suction cup 534A at the foremost end is in contact with the support plate 11 first. As the mounting base 533 continues rotating, the elastic pressing head 535A close to the elastic vacuum suction cup 534A at the foremost end is in point contact with the adhesive layer 12, the mounting base 533 continues rotating, and the contact area between the elastic pressing head 535A and the adhesive layer 12 expands from point to surface, thereby completing the lamination of the adhesive layer 12 on the support plate 11 with the base layer 13 of the microneedle patch 121. Then, the elastic vacuum suction cup 534A at the foremost end is opened. Since the abutting surface 5341 of the elastic vacuum suction cup 534A protrudes out of the lamination surface 5351, away from the rotary table 532, of the elastic pressing head 535A in the radial direction of the rotary table 532, when the elastic pressing head 535A is completely laminated on the adhesive layer 12, the elastic vacuum suction cup 534A is still pressed on the surface of the support plate 11, so that the elastic vacuum suction cup 534A can adsorb the support plate 11 to perform the separation operation, that is, as the mounting base 533 rotates to drive the support plate 11 and the microneedle patch 131 adhered to a position, corresponding to the elastic pressing head 535A at the foremost end, on the support plate 11 to be demolded, so that the microneedle patch 131 is completely separated from the female mold 7. At the same time, the elastic vacuum suction cup 534B in the middle is pressed on the support plate 11. Due to the pressing effect of the elastic vacuum suction cup 534B in the middle, even if the elastic vacuum suction cup 534A at the foremost end adsorbs the support plate 11, the support plate 11 behind the middle elastic vacuum suction cup 534B can still be pressed against the carrier 6. At this time, the second elastic pressing head 535B is in point contact with the adhesive layer 12. As the mounting base 533 continues rotating, after the second elastic pressing head 535B completes the lamination, the second elastic vacuum suction cup 534B is opened and adsorbs the support plate 11 to drive the microneedle patch 132 next to the rear end thereof to be demolded. When the demolding of the microneedle patch 132 next to the second elastic vacuum suction cup 534B is completed, the third elastic vacuum suction cup 534C next to same is opened, and the three elastic vacuum suction cups 534A, 534B and 534C simultaneously adsorb the support plate 11. As the mounting base 533 rotates, the support plate 11 adhered with the microneedle patches 131 and 132 is conveyed to the next process.

The microneedle patch base layer lamination and separation device 5 in the embodiment achieves the simultaneous microneedle lamination and demolding operations of the plurality of microneedle patches adhered to the same support plate 11, thereby improving the production efficiency. At the same time, a production device is integrated, so that the occupied space of the device and the occupied space of the production line are reduced, and the production cost is reduced.

Second embodiment of microneedle patch base layer lamination and separation device:

As an illustration of a second embodiment of the microneedle patch base layer lamination and separation device of the present disclosure, only the differences from the first embodiment of the microneedle patch base layer lamination and separation device are described below.

Figure 16:
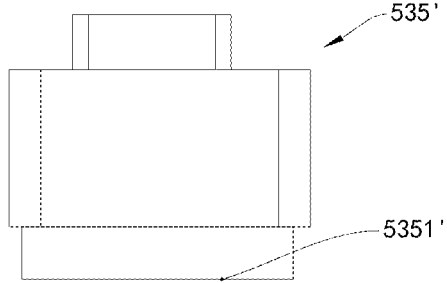
FIG. 16 is a front view of an elastic pressing head in a second embodiment of a microneedle patch base layer lamination and separation device of the present disclosure.
Figure 17:
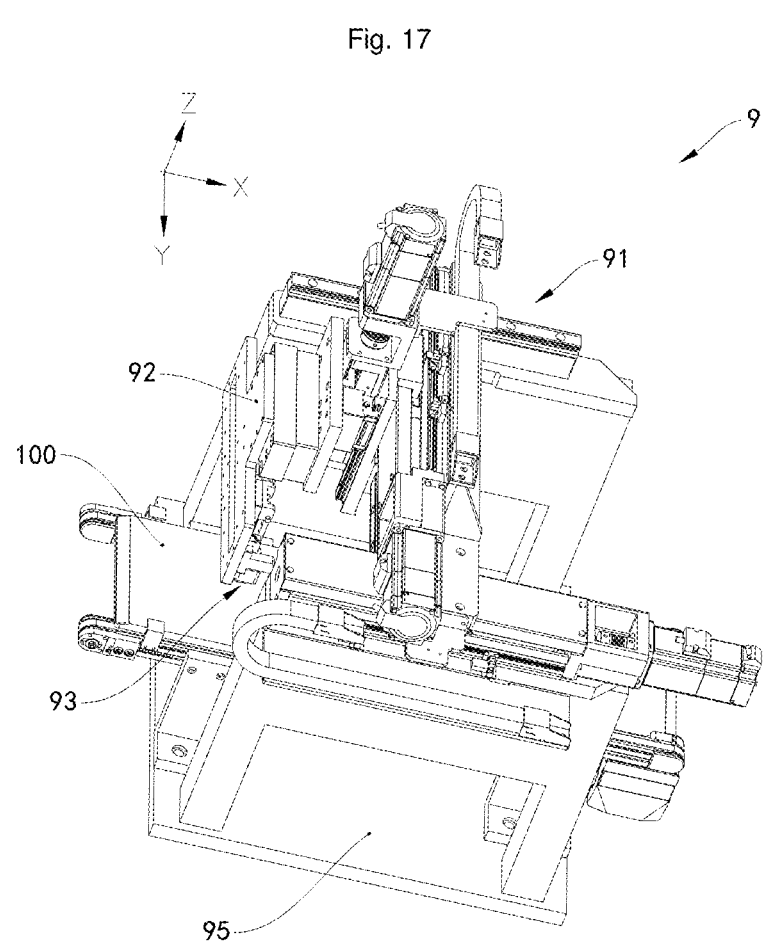
FIG. 17 is a structural diagram of a first embodiment of a microneedle patch base layer lamination device of the present disclosure.
Figures 18, 19:
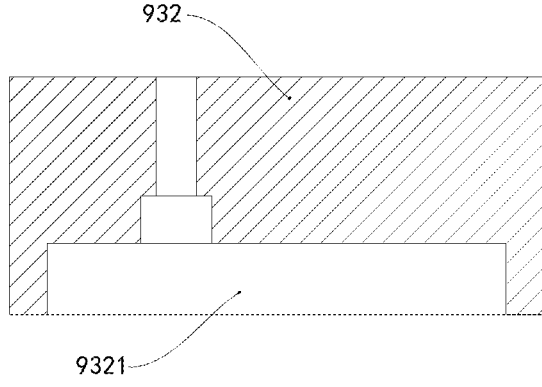
FIG. 18 is a structural diagram of a lamination apparatus in a first embodiment of a microneedle patch base layer lamination device of the present disclosure.
FIG. 19 is a section view of an implementation of a drive seat in a first embodiment of a microneedle patch base layer lamination device of the present disclosure.

Referring to FIG. 16, the lamination surface 5351' of the elastic pressing head 535' in the embodiment is arranged as a horizontally extended plane, and the lamination surface 5351' of the elastic pressing head 535' is tangent to the peripheral wall of the rotary table 532.

Since the rotary table 532 drives the elastic pressing head 535' to rotate around the horizontal direction, the horizontally extended lamination surface 5351' is pressed against the position, corresponding to the accommodating hole 111 of the support plate 11, of the adhesive layer 12 at an angle relative to the vertical direction, that is, when the horizontally extended lamination surface 5351' just abuts against the adhesive layer 12, the horizontally extended lamination surface 5351' forms a line contact with the product to be laminated, there is still a certain distance between the adhesive layer 12 outside a contact line and the base layer 13 in the vertical direction, and the contact area of the line contact is relatively small, so that the introduction of bubbles at the line contact position can be effectively avoided. As the rotation control mechanism 531 continues controlling the rotary table 532 to rotate in the horizontal direction and the movement control mechanism 51 continues controlling the movable seat 52 or the carrier 6 to move in the horizontal direction, the horizontally extended lamination surface 5351' of the elastic pressing head 535' increases the downward pressure force on the adhesive layer 12 in the vertical direction and performs the pressure maintaining operation, and the lamination area of the horizontally extended lamination surface 5351' gradually expands from the line contact in the horizontal direction. The actual lamination area of the horizontally extended lamination surface 5351' after elastic deformation is not less than the adhesion area between the base layer 13 of the microneedle patch and the adhesive layer 12, which can ensure that the horizontally extended lamination surface 5351' is elastically deformed outward in the horizontal direction from line to surface and is pressed against the product to be laminated, so that bubbles in the laminated product are effectively and completely discharged from the horizontally extended lamination surface 5351' in the horizontal direction from one side to the other side, thereby avoiding the possibility of bubbles formed between the adhesive layer 12 and the base layer 13 of the microneedle patch.

First embodiment of microneedle patch base layer lamination device:

Referring to FIG. 17 to FIG. 21, the embodiment discloses a microneedle patch base layer lamination device 9, including a rack 95, a movement control mechanism 91, a movable seat 92, and a lamination apparatus 93. The lamination apparatus 93 is arranged on the movable seat 92, a carrier 100 is supported on the rack 95, the movement control mechanism 91 is arranged on the rack 95 and may control the movable seat 92 and/or the carrier 100 to move in a vertical direction and a horizontal direction respectively, and the carrier 100 is configured to place a female mold filled and cured to form a microneedle patch and a support plate 11. The lamination apparatus 93 in the embodiment includes a pressure maintaining control mechanism and an elastic pressing head 936. The elastic pressing head 936 may be located above the carrier 100 in the vertical direction, the pressure maintaining control mechanism may control the elastic pressing head 936 to move in the vertical direction, and a lamination surface 9361, close to the carrier 100, of the elastic pressing head 936 in the vertical direction is arranged as a quadratic surface. The lamination surface 9361 of the elastic pressing head 936 is bent away from the carrier 100, so that after the elastic pressing head 936 is elastically deformed, the actual lamination area of the quadratic lamination surface 9361 of the elastic pressing head 936 to the product to be laminated is greater than the adhesion area of the adhesive layer 12 adhered between the base layer 13 of the microneedle patch and the support plate 11.

The female mold filled with a raw material solution and cured to form the microneedle patch is placed on the carrier 100, and the support plate 11 adhered with the adhesive layer 12 is placed at a corresponding position on the female mold, so that the accommodating hole 111 of the support plate 11 matches the position of the base layer 13 of the microneedle patch on the female mold, but has a certain distance in the vertical direction, thereby forming the product to be laminated on the carrier 100 of the microneedle patch base layer lamination device 9 in the embodiment.

In order to adhere the support plate 11 to the base layer 13 of the microneedle patch through the adhesive layer 12, the movement control mechanism 91 of the microneedle patch base layer lamination device 9 in the embodiment controls the movable seat 92 to drive the lamination apparatus 93 to move in the horizontal direction, and/or, the movement control mechanism 91 controls the carrier 100 to move in the horizontal direction, so that the elastic pressing head 936 of the lamination apparatus 93 is located above the product to be laminated of the carrier 100 in the vertical direction, and then the movement control mechanism 91 controls the movable seat 92 to drive the lamination apparatus 93 to move downward in the vertical direction, and/or, the movement control mechanism 91 controls the carrier 100 to move upward in the vertical direction, so that the lamination surface 9361 of the elastic pressing head 936 of the lamination apparatus 93 is pressed against the adhesive layer 12 of the product to be laminated, that is, the elastic pressing head 936 of the lamination apparatus 93 is pressed against the position, corresponding to the accommodating hole 111, of the adhesive layer 12 to perform a lamination operation, and then the pressure maintaining control mechanism of the lamination apparatus 93 controls the elastic pressing head 936 to move downward in the vertical direction, so that the lamination surface 9361 of the elastic pressing head 936 laminates the adhesive layer 12 of the product to be laminated with the base layer 13 of the microneedle patch to perform a pressure maintaining operation, thereby automatically completing the lamination and adhesion between the microneedle patch and the adhesive layer 12, with a high degree of automation.

Since the elastic pressing head 936 in the embodiment has an elastic deformation capability, the elastic pressing head 936 can be deformed in the process of moving downward in the vertical direction to apply pressure to the product to be laminated, so as to avoid rigid collision between the elastic pressing head 936 and the product to be laminated, protect the microneedle patch and the adhesive layer 12, and avoid the microneedle patch and the adhesive layer 12 from being pressed into defects such as gravure, embossing, and irreversible deformation, thereby improving the yield rate.

In the embodiment, the lamination surface 9361 of the elastic pressing head 936, which is close to the carrier 100 in the vertical direction, is arranged as a quadratic surface, and the quadratic surface at least includes a cylindrical surface, an elliptical cylindrical surface, a parabolic cylindrical surface, a spherical surface, an ellipsoidal surface, an elliptical paraboloid, etc. The lamination surface 9361 of the elastic pressing head 936 is bent away from the carrier 100. Referring to FIG. 22 to FIG. 24, since the quadratic lamination surface 9361 of the elastic pressing head 936 in the first implementation is bent away from the carrier 100 in an arc shape, and since the adhesive layer 12 on the support plate 11 and the base layer 13 of the microneedle patch on the female mold have a certain distance in the vertical direction, when the lamination surface 9361 of the elastic pressing head 936 is just pressed against the product to be laminated, that is, when the quadratic lamination surface 9361 of the elastic pressing head 936 just abuts against the position, corresponding to the accommodating hole 111, of the adhesive layer 12, the lowest end in the middle of the quadratic lamination surface 9361 forms a point contact with the product to be laminated, and then is pressed against the adhesive layer 12 to form a point contact with the base layer 13. There is still a certain distance between the adhesive layer 12 and the base layer 13 outside the contact point in the vertical direction, and the contact area of the point contact between the adhesive layer 12 and the base layer 13 is relatively small, so that the introduction of bubbles at the point contact position can be effectively avoided. As the elastic pressing head 936 continues laminating downward and maintaining pressure in the vertical direction, the lamination area of the quadratic lamination surface 9361 gradually expands from the contact point in the radial direction. The actual lamination area of the quadratic lamination surface 9361 after elastic deformation is not less than the adhesion area between the base layer 13 of the microneedle patch and the adhesive layer 12, which can ensure that the quadratic lamination surface 9361 is elastically deformed outward in the radial direction from point to surface and is pressed against the product to be laminated, so that bubbles in the laminated product are effectively and completely discharged from the quadratic lamination surface 9361 in the radial direction from inside to outside, thereby avoiding the possibility of bubbles between the adhesive layer 12 and the base layer 13 of the microneedle patch.

In addition, since the microneedle patch is located on the female mold, the microneedle array is located in a microneedle forming groove of the female mold, and the base layer 13 of the microneedle patch is supported by the female mold. In the embodiment, the female mold is made of a PDMS material, so that the female mold has a certain elastic deformation capability, but the elastic deformation capability of the female mold is less than that of the elastic pressing head 936. The microneedle array of the microneedle patch is supported by the microneedle forming groove of the female mold, which can ensure that the microneedle array of the microneedle patch cannot be damaged by an external force when the elastic pressing head 936 laminates the adhesive layer 12 and the base layer 13, so as to achieve the integrity of the microneedle patch.

In the process of preparing the microneedle patch, an outer surface of the base layer 13 is not very smooth due to the inconsistency of the shrinkage of the microneedle raw material solution filled on the female mold after drying, thereby increasing the process difficulty of bubble-free lamination of the adhesive layer 12 and the base layer 13. The microneedle patch base layer lamination device 9 in the embodiment is designed with the female mold, the base layer 13, the adhesive layer 12, and the elastic pressing head 936 all having the elastic deformation capabilities, when the adhesive layer 12, the base layer 13, and the female mold are in contact due to the lamination of the elastic pressing head 936, the deformations of various elements may compensate for each other, thereby solving the problem of bubble-free lamination caused by the uneven outer surface of the existing base layer 13, so that the base layer 13 can be tightly laminated with the adhesive layer 12 to better achieve bubble-free lamination. Even if a slight inclination of the elastic pressing head 936 or a small amount of deviation of alignment of the elastic pressing head 936 and the adhesive layer 12 is caused by an external force during the lamination operation, bubble-free lamination of the base layer 13 and the adhesive layer 12 may still be achieved, the yield rate of the product is improved, and the precision control of the device may be reduced, thereby reducing the production cost.

When performing lamination on the adhesive layer 12 and the base layer 13 of the microneedle patch, the elastic pressing head 936 only moves downward in the vertical direction. The base layer 13 of the microneedle patch is supported by the female mold. Since the elastic deformation capability of the female mold is less than that of the elastic pressing head 936, the rigidity of the female mold is greater than that of the elastic pressing head 936, the elastic pressing head 936 is elastically deformed under a reaction force of the female mold, so as to avoid the excessive compressive deformation of the female mold when the elastic pressing head 936 moves downward, thereby effectively avoiding the base layer 13 of the microneedle patch from being deformed by the force in the vertical direction, and ensuring the yield rate of the product. In addition, in the process of laminating the adhesive layer 12 and the base layer 13 of the microneedle patch, the elastic pressing head 936 only moves in the vertical direction and does not move in the horizontal direction, which may avoid the elastic pressing head 936 from moving in the horizontal direction and dragging the base layer 13 to deform due to the friction between the elastic pressing head 936 and the base layer 13 of the microneedle patch, thereby reducing the precision control of the device, and at the same time reducing the process difficulty of bubble-free lamination of the adhesive layer 12 and the base layer 13 of the microneedle patch, improving the yield rate of the product, reducing the production cost, and saving energy and protecting the environment.

Therefore, the microneedle patch base layer lamination device 9 in the embodiment has a high degree of automation, stable and reliable operation, high yield rate, high production efficiency, and low production cost. The elastic pressing head 936 in the embodiment is particularly suitable for lamination of the base layer 13 of a circular microneedle patch and the adhesive layer 12.

Figure 26:
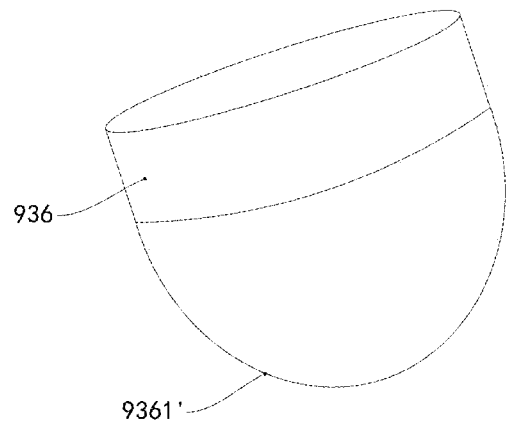
FIG. 26 is a structural diagram of a third implementation of an elastic pressing head in a first embodiment of a microneedle patch base layer lamination device of the present disclosure.

In order to further improve the operational reliability of the elastic pressing head 936, the lamination surface 9361' of the elastic pressing head 936 in the embodiment is arranged as a spherical surface (Referring to FIG. 26), or the lamination surface 9361 of the elastic pressing head 936 is arranged as an ellipsoidal surface.

In order to improve the operational reliability and stability of the lamination apparatus 93, the lamination apparatus 93 in the embodiment further includes a drive seat 932. The pressure maintaining control mechanism may control the drive seat 932 to move in the vertical direction, and the elastic pressing head 936 is arranged on the drive seat 932. Further, in the embodiment, a slide rail 934 protrudes out of the movable seat 92, the slide rail 934 extends in the vertical direction, the drive seat 932 is provided with a chute, and the chute may be slidably matched with the slide rail 934 in the vertical direction, so that the drive seat 932 can slide smoothly. The pressure maintaining control mechanism in the embodiment is a pressure maintaining cylinder 933, the pressure maintaining cylinder 933 is mounted on the movable seat 92, and a piston rod of the pressure maintaining cylinder 933 extends in the vertical direction and is connected to the drive seat 932, so that the pressure maintaining cylinder 933 drives the elastic pressing head 936 to move in the vertical direction. Since drive seat 932 may move in the vertical direction along the slide rail 934, it is ensured that the elastic pressing head 936 may move accurately in the vertical direction when laminating downward, and does not deviate due to the action of an external force, thereby ensuring the stability of lamination and ensuring bubble-free lamination of the base layer 13 and the adhesive layer 12.

An end surface, close to the carrier 100, of the drive seat 932 in the embodiment in the vertical direction is provided with an accommodating groove 9321. The elastic pressing head 936 may be made of an elastic material with uniform performance, and is partially embedded in the accommodating groove 9321. In the embodiment, the elastic pressing head 936 includes a mounting part 9362, a connecting part 9363, and a lamination part 9364 which are connected in sequence. The lamination surface 9361 is located on the lamination part 9364, and the mounting part 9362, away from the lamination surface 9361, of the elastic pressing head 936 in the vertical direction is embedded in the accommodating groove 9321. In some embodiments, a mounting end surface 93621 of the mounting part 9362 of the elastic pressing head 936 in the embodiment is glued to a concave bottom surface of the accommodating groove 9321, which can achieve the purpose of quick mounting and conveniently replacing the elastic pressing head 936. The mounting end surface 93621 of the mounting part 9362 of the elastic pressing head 936 is arranged as a smooth surface in the horizontal direction, and correspondingly, the concave bottom surface of the accommodating groove 9321 of the drive seat 932 is also arranged as a smooth surface in the horizontal direction. The mounting end surface 93621 of the mounting part 9362 of the elastic pressing head 936 is adaptively laminated with the concave bottom surface of the accommodating groove 9321, which limits the movement of the elastic pressing head 936 relative to the drive seat 932 in the horizontal direction, thereby improving the stability and firmness of mounting between the drive seat 932 and the elastic pressing head 936.

The elastic pressing head 936 is made of an elastic material. In the embodiment, the specific material combination of the elastic pressing head 936 is the same as that of the elastic pressing head 535 in the first embodiment of the microneedle patch base layer lamination and separation device, so that the elastic pressing head 936 can achieve automatic elastic pressure lamination after being deformed by force, and the elastic pressing head 936 can restore the deformation after the external force is released. Moreover, the elastic pressing head 936 has good surface gloss, does not damage the surface of the product, and is good in chemical stability, environmentally friendly and non-toxic, and safe to use.

In order to further improve the operational stability and reliability of the microneedle patch base layer lamination device 9 in the embodiment to ensure the production quality of the product, and further improve the degree of automation, the structure and working principle of the movement control mechanism 91 in the embodiment are the same as those of the movement control mechanism 21 in the first embodiment of the microneedle patch and demolding separation device.

A control method for the microneedle patch base layer lamination device 9 in the embodiment includes that: the movement control mechanism 91 controls the movable seat 92 to drive the lamination apparatus 93 to move in the horizontal direction, and/or, the movement control mechanism 91 controls the carrier 100 to drive the product to be laminated to move in the horizontal direction, so that the elastic pressing head 936 of the lamination apparatus 93 is located above the product to be laminated on the carrier 100 in the vertical direction; the movement control mechanism 91 controls the movable seat 92 to drive the lamination apparatus 93 to move downward in the vertical direction, and/or, the movement control mechanism 91 controls the carrier 100 to drive the product to be laminated to move upward in the vertical direction, so that the lamination surface 9361 of the elastic pressing head 936 of the lamination apparatus 93 is pressed against the adhesive layer 12 of the product to be laminated; the pressure maintaining control mechanism of the lamination apparatus 93 controls the elastic pressing head 936 to move downward in the vertical direction, so that the lamination surface 9361 of the elastic pressing head 936 laminates the adhesive layer 12 of the product to be laminated and the base layer 13 of the microneedle patch to perform the pressure maintaining operation; after the elastic pressing head 936 completes the lamination operation, the pressure maintaining control mechanism of the lamination apparatus 93 controls the elastic pressing head 936 to move upward in the vertical direction to reset, and the movement control mechanism 91 controls the movable seat 92 to drive the lamination apparatus 93 to move upward in the vertical direction to reset, and/or, the movement control mechanism 91 controls the carrier 100 to drive the laminated product to move downward in the vertical direction; and the movement control mechanism 91 controls the movable seat 92 to drive the lamination apparatus 93 to move to above the next product to be laminated in the horizontal direction, and/or, the movement control mechanism 91 controls the carrier 100 to drive the next product to be laminated to move to below the lamination apparatus 93 in the horizontal direction, and then the above lamination step is repeated.

Referring to FIG. 23, a projection area of the quadratic lamination surface 9361 of the elastic pressing head 936 in the embodiment in the horizontal direction is greater than or equal to the adhesion area to be laminated between the adhesive layer 12 of the product to be laminated and the base layer 13. When the projection area of the quadratic lamination surface 9361 of the elastic pressing head 936 in the horizontal direction is equal to the adhesion area to be laminated between the adhesive layer 12 of the product to be laminated and the base layer 13, the overall volume of the elastic pressing head 936 may be minimized, so that on the one hand, the occupied space of the device is reduced and as many elastic pressing heads 936 as possible may be provided under the same operation space condition, and on the other hand, the energy consumption of the single elastic pressing head 936 is reduced, energy is saved and the environment is protected, and the production cost is reduced. Moreover, a contact point when the lamination surface 9361 of the elastic pressing head 936 in the embodiment is just pressed against the adhesive layer 12 is a contact point A, and the contact point A is a contact point between the corresponding adhesive layer 12 and the base layer 13. The maximum arc contact point after the lamination surface 9361 of the elastic pressing head 936 is completely laminated with the adhesive layer 12 is a contact point B, an angle between a connecting line between the contact point A and the contact point B and the horizontal direction is θ, and 26°≤θ≤42°. When θ<26°, after the lamination surface 9361 of the elastic pressing head 936 is completely laminated with the adhesive layer 12, the actual lamination area of the quadratic lamination surface 9361 of the elastic pressing head 936 after elastic deformation is less than the required adhesion area between the base layer 13 of the microneedle patch and the adhesive layer 12, so that the lamination and adhesion between the base layer 13 and the adhesive layer 12 cannot be covered, the positions of the base layer 13 and the adhesive layer 12 outside the lamination and adhesion area cannot be laminated, the contact is not firm and bubbles are generated, thereby forming defective products. When θ>42°, the elastic pressing head 936 is just in contact with the adhesive layer 12 to press the adhesive layer 12 to be in contact with the base layer 13, so that the contact area between the adhesive layer 12 and the base layer 13 is too large, and the bubbles are introduced into the contact point, resulting in unqualified laminated products.

Figure 27:
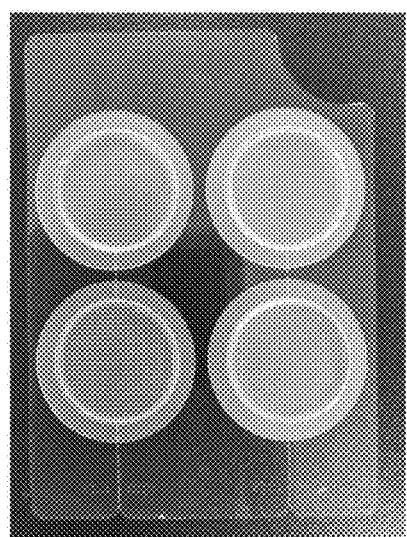
FIG. 27 is a lamination effect diagram when an angle between a connecting line between a contact point A and a contact point B of a lamination surface of an elastic pressing head in a first embodiment of a microneedle patch base layer lamination device of the present disclosure and a horizontal direction is 26°.
Figure 28:
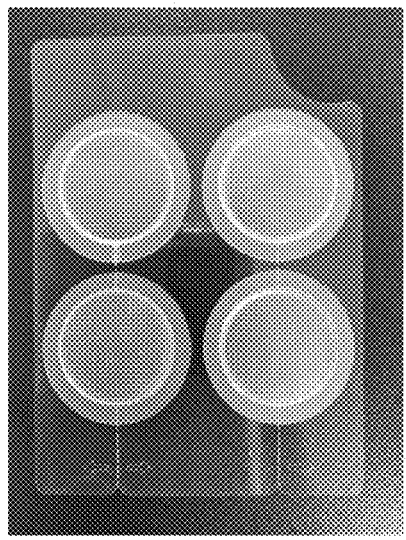
FIG. 28 is a lamination effect diagram when an angle between a connecting line between a contact point A and a contact point B of a lamination surface of an elastic pressing head in a first embodiment of a microneedle patch base layer lamination device of the present disclosure and a horizontal direction is 30°.
Figure 29:
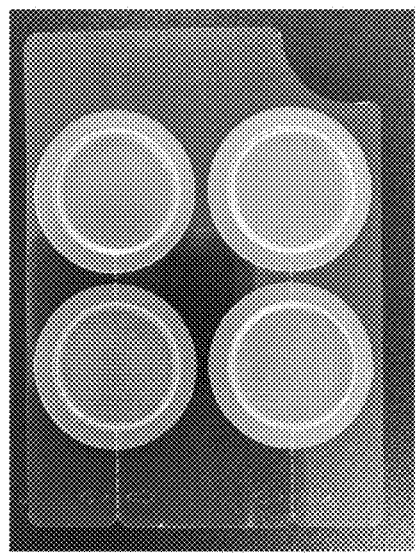
FIG. 29 is a lamination effect diagram when an angle between a connecting line between a contact point A and a contact point B of a lamination surface of an elastic pressing head in a first embodiment of a microneedle patch base layer lamination device of the present disclosure and a horizontal direction is 35°.
Figure 30:
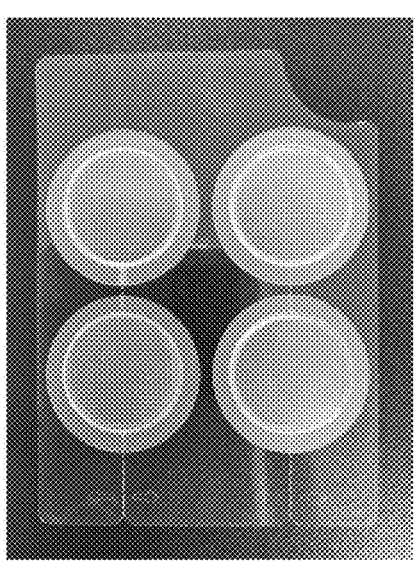
FIG. 30 is a lamination effect diagram when an angle between a connecting line between a contact point A and a contact point B of a lamination surface of an elastic pressing head in a first embodiment of a microneedle patch base layer lamination device of the present disclosure and a horizontal direction is 42°.

Referring to FIG. 27 to FIG. 30. FIG. 27 is a lamination effect diagram when an angle θ between a connecting line between a contact point A and a contact point B of a lamination surface 9361 of an elastic pressing head 936 and a horizontal direction is 26°, FIG. 28 is a lamination effect diagram when an angle θ between a connecting line between a contact point A and a contact point B of a lamination surface 9361 of an elastic pressing head 936 and a horizontal direction is 30°, FIG. 29 is a lamination effect diagram when an angle θ between a connecting line between a contact point A and a contact point B of a lamination surface 9361 of an elastic pressing head 936 and a horizontal direction is 35°, and FIG. 30 is a lamination effect diagram when an angle θ between a connecting line between a contact point A and a contact point B of a lamination surface 9361 of an elastic pressing head 936 and a horizontal direction is 42°. It can be seen from the lamination effect diagrams of FIG. 27 to FIG. 30 that the angle θ between the connecting line between the contact point A and the contact point B of the quadratic lamination surface 9361 of the elastic pressing head 936 and the horizontal direction satisfies 26°≤θ≤42°, which can effectively and completely discharge the gas between the adhesive layer 12 and the base layer 13 of the microneedle patch, thereby avoiding the possibility of bubbles between the adhesive layer 12 and the base layer 13 of the microneedle patch, ensuring that defective products cannot be caused by the existence of bubbles between the microneedle patch and the adhesive layer 12, then improving the yield rate, and enhancing the adhesion stability between the microneedle patch and the support plate 11, so that the microneedle patch can be firmly supported by the support plate 11.

Further, the number of lamination apparatuses 93 in the embodiment is at least two, and the plurality of lamination apparatuses 93 are arranged side by side on the movable seat 92 in the horizontal direction. Specifically, the plurality of lamination apparatuses 93 in the embodiment are arranged side by side on the movable seat 92 in a Y-axis direction.

Figure 25:
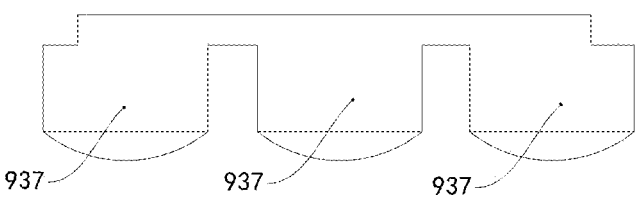
FIG. 25 is a front view of a second implementation of an elastic pressing head in a first embodiment of a microneedle patch base layer lamination device of the present disclosure.

Referring to FIG. 25, which is a second implementation of the elastic pressing head 937. Specifically, the number of elastic pressing heads 937 is at least two, the plurality of elastic pressing heads 937 are arranged side by side in the horizontal direction, and the two adjacent elastic pressing heads 937 are connected. The pressure maintaining control mechanism may control the plurality of elastic pressing heads 937 to move synchronously in the vertical direction. Specifically, the plurality of elastic pressing heads 937 in the second implementation are arranged side by side in a Y-axis direction to form an integrated design, which facilitates the mounting and dismounting of the elastic pressing heads 937, thereby improving the production efficiency.

Second embodiment of microneedle patch base layer lamination device:

As an illustration of a second embodiment of the microneedle patch base layer lamination device of the present disclosure, only the differences from the first embodiment of the microneedle patch base layer lamination device are described below.

Figure 31:
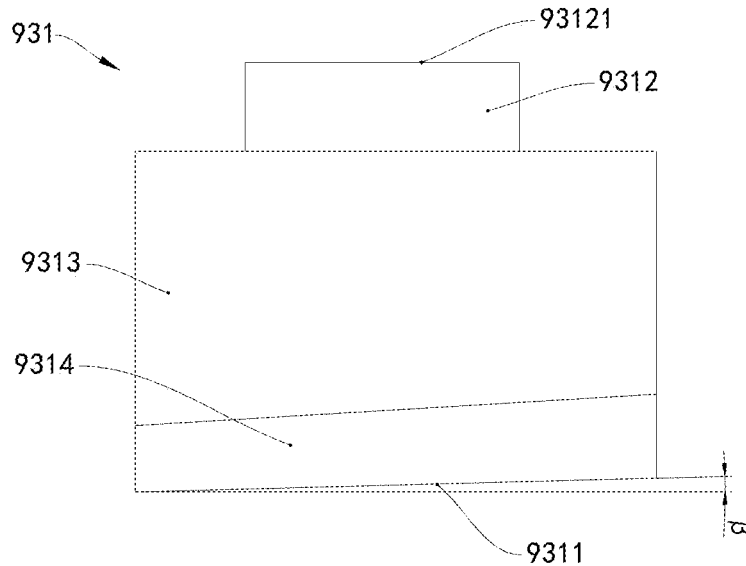
FIG. 31 is a front view of an elastic pressing head in a second embodiment of a microneedle patch base layer lamination device of the present disclosure.
Figure 32:
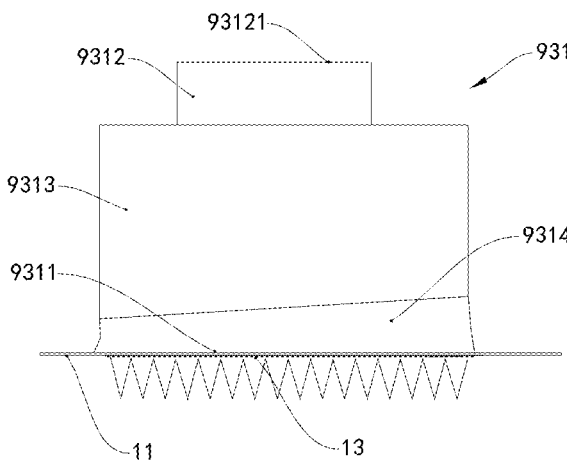
FIG. 32 is a front view of an operating state of an elastic pressing head in a second embodiment of a microneedle patch base layer lamination device of the present disclosure.
Figure 33:
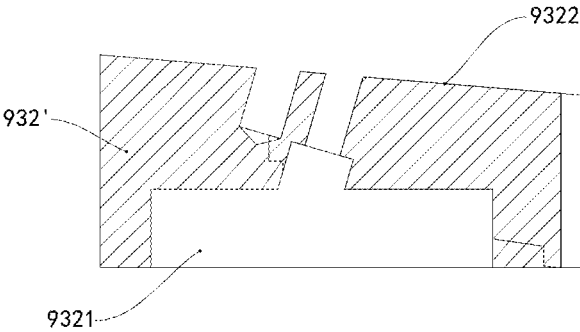
FIG. 33 is a section view of another implementation of a drive seat in a second embodiment of a microneedle patch base layer lamination device of the present disclosure.
Figure 34:
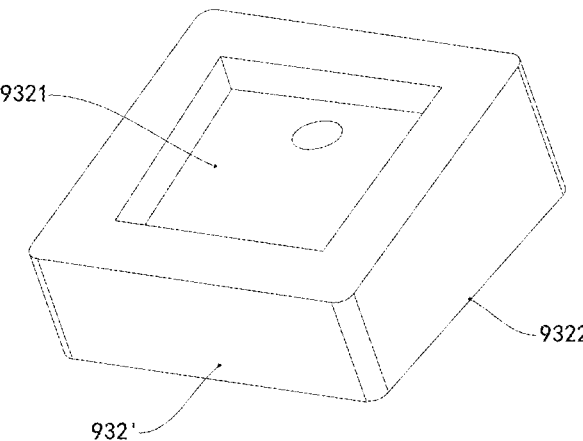
FIG. 34 is a structural diagram of another implementation of a drive seat in a second embodiment of a microneedle patch base layer lamination device of the present disclosure.
Figure 37:
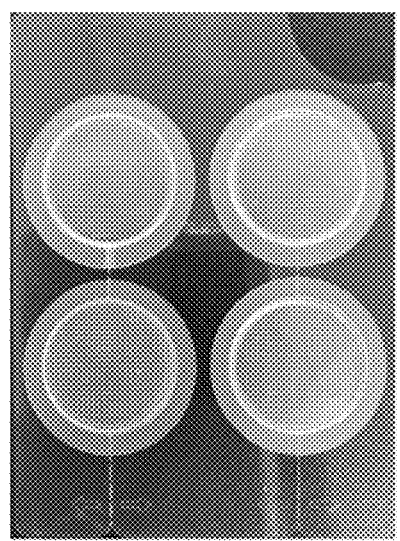
FIG. 37 is a lamination effect diagram when an inclination angle between a lamination surface of an elastic pressing head in a second embodiment of a microneedle patch base layer lamination device of the present disclosure and a horizontal direction is 1°.

Referring to FIG. 31 and FIG. 32, in the embodiment, the lamination surface 9311, close to the carrier 100, of the elastic pressing head 931 in the vertical direction is inclined relative to the horizontal direction, so that after the elastic pressing head 931 is elastically deformed, the actual lamination area of the inclined lamination surface 9311 of the elastic pressing head 931 on the product to be laminated is greater than or equal to the adhesion area between the base layer 13 of the microneedle patch and the adhesive layer 12 on the support plate 11.

In the embodiment, the lamination surface 9311, close to the carrier 100, of the elastic pressing head 931 in the vertical direction is inclined relative to the horizontal direction. Since the adhesive layer 12 on the support plate 11 and the base layer 13 of the microneedle patch on the female mold have a certain distance in the vertical direction, when the lamination surface 9311 of the elastic pressing head 931 is just pressed against the product to be laminated, that is, when the lowest end of the inclined lamination surface 9311 of the elastic pressing head 931 just abuts against the adhesive layer 12 at a position corresponding to the boundary of the accommodating hole 111, the lowest end of the inclined lamination surface 9311 forms a line contact with the adhesive layer 12 next to the boundary of the accommodating hole 111, and then is pressed against the adhesive layer 12 to correspondingly form a line contact between the adhesive layer 12 and the base layer 13. The adhesive layer 12 and the base layer 13 outside the contact line still have a certain distance in the vertical direction, and the contact area of the line contact between the adhesive layer 12 and the base layer 13 is relatively small, so that the introduction of bubbles at the line contact position can be effectively avoided. As the elastic pressing head 931 continues laminating downward and maintaining pressure in the vertical direction, the lamination area of the inclined lamination surface 9311 gradually expands from the line contact in the inclined direction of the lamination surface 9311. The actual lamination area of the lamination surface 9361 after elastic deformation is not less than the actual adhesion area between the base layer 13 of the microneedle patch and the adhesive layer 12, which can ensure that the lamination surface 9311 is elastically deformed in the inclined direction thereof from line to surface and is pressed against the product to be laminated, so that bubbles in the laminated product can be effectively and completely discharged from the inclined direction of the lamination surface 9311, thereby avoiding the possibility of bubbles between the adhesive layer 12 and the base layer 13 of the microneedle patch, ensuring that defective products cannot be caused by the existence of bubbles between the base layer 13 of the microneedle patch and the adhesive layer 12, improving the production yield rate, and enhancing the adhesion stability between the base layer 13 of the microneedle patch and the support plate 11, so that the microneedle patch can be firmly supported by the support plate 11. The elastic pressing head 931 in the embodiment is particularly suitable for lamination of the base layer 13 of an arc-shaped microneedle patch and the adhesive layer 12.

In the embodiment, the elastic pressing head 931 includes a mounting part 9312, a connecting part 9313, and a lamination part 9314 which are connected in sequence. The lamination surface 9311 is located on the lamination part 9314, and the mounting part 9312, away from the lamination surface 9311, of the elastic pressing head 931 in the vertical direction is embedded in the accommodating groove 9321 of the drive seat 932. In one implementation, a mounting manner between a mounting end surface 93121 of the mounting part 9312 of the elastic pressing head 931 and the accommodating groove 9321 is the same as that between a mounting end surface 93621 of the mounting part 9362 of the elastic pressing head 936 and the accommodating groove 9321 in the first embodiment of the microneedle patch base layer lamination device.

Referring to FIG. 33 to FIG. 36, which are another implementation of the drive seat 932' and another implementation of the elastic pressing head 931' in the embodiment. The vertical cross section of the drive seat 932' is wedge-shaped, that is, the mounting end surface 9322 away from the accommodating groove 9321 in the vertical direction is inclined relative to the horizontal direction. When the drive seat 932' is mounted on the lamination device, the mounting end surface 9322 of the drive seat 932' extends horizontally, and the accommodating groove 9321 for mounting the elastic pressing head 931' is inclined relative to the horizontal direction. Correspondingly, the mounting end surface 93121 of the elastic pressing head 931' is inclined relative to the horizontal direction, so that the lamination surface 9311' originally arranged as a smooth surface in the horizontal direction is inclined relative to the horizontal direction, that is, when the elastic pressing head 931' is mounted on the drive seat 932', the lamination surface 9311' of the elastic pressing head 931' is inclined relative to the horizontal direction.

In addition, in a third implementation of the drive seat and the elastic pressing head, the drive seat 932 may also be provided with the concave accommodating groove 9321, a mounting surface of the accommodating groove 9321 is inclined to the horizontal plane, and the mounting end surface 93121 of the elastic pressing head 931 is fixed to the mounting surface of the accommodating groove 9321, so that the lamination surface 9311, close to the carrier 100, of the elastic pressing head 931 in the vertical direction is inclined relative to the horizontal direction.

The drive seat 932 and the elastic pressing head 931 of the present disclosure may be in any other form to mount the drive seat 932 on the lamination device, and after the elastic pressing head 931 is mounted on the drive seat 932, it is only necessary to ensure that the lamination surface 9311, close to the carrier 100, of the elastic pressing head 931 after mounting in the vertical direction is inclined relative to the horizontal direction.

In each implementation of the elastic pressing heads 931 and 931', in some embodiments, the inclination angle $\beta$ between the lamination surfaces 9311 and 9311' of the elastic pressing heads 931 and 931' and the horizontal direction is between 1° and 13°. The projection area of the inclined lamination surfaces 9311 and 9311' of the elastic pressing heads 931 and 931' in the horizontal direction is greater than or equal to the adhesion area between the base layer 13 of the microneedle patch and the adhesive layer 12. When $\beta < 1°$, and the elastic pressing heads 931 and 931' move downward to be just in contact with the adhesive layer 12 to press the adhesive layer 12 to be in contact with the base layer 13, so that the contact area between the adhesive layer 12 and the base layer 13 is relatively large, and bubbles are easily introduced by the relatively large contact area, resulting in a low yield rate. When $\beta > 13°$, and the elastic pressing heads 931 and 931' move downward to no longer be deformed, the actual lamination area is still smaller than the required lamination area between the base layer 13 of the microneedle patch and the adhesive layer 12, so that the base layer 13 of the microneedle patch and the adhesive layer 12 cannot be completely laminated, bubbles exist, and defective products are caused. In addition, since the projection area of the inclined lamination surfaces 9311 and 9311' of the elastic pressing heads 931 and 931' in the horizontal direction is greater than or equal to the required lamination area between the base layer 13 of the microneedle patch and the adhesive layer 12, the volume of the device is minimized, and as many elastic pressing heads 931 and 931' as possible are provided under the same volume, thereby reducing the requirements for the factory space, and reducing the production cost.

Figure 38:
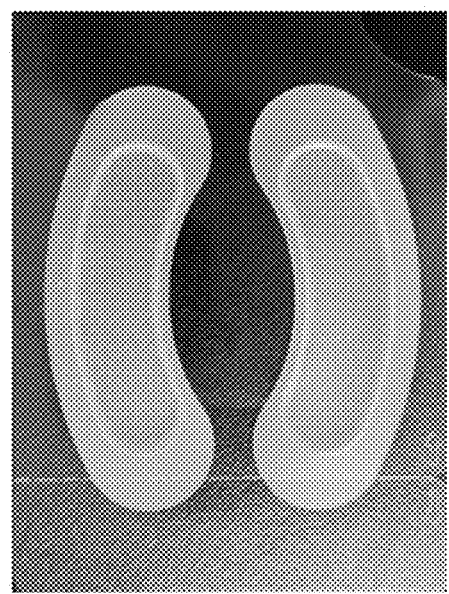
FIG. 38 is a lamination effect diagram when an inclination angle between a lamination surface of an elastic pressing head in a second embodiment of a microneedle patch base layer lamination device of the present disclosure and a horizontal direction is 5°.
Figure 39:
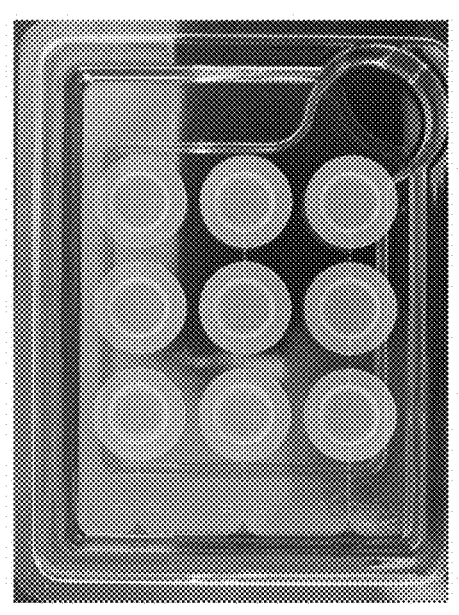
FIG. 39 is a lamination effect diagram when an inclination angle between a lamination surface of an elastic pressing head in a second embodiment of a microneedle patch base layer lamination device of the present disclosure and a horizontal direction is 9°.
Figure 40:
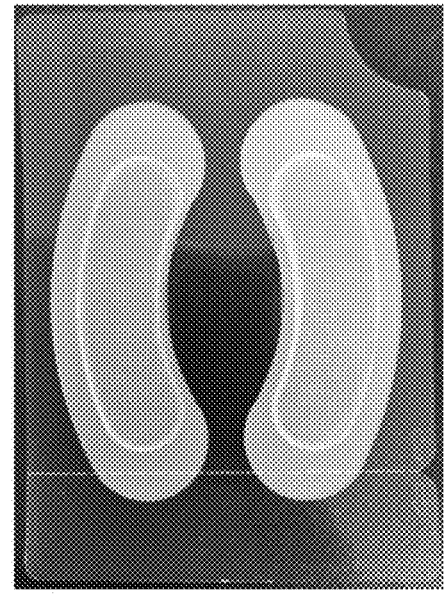
FIG. 40 is a lamination effect diagram when an inclination angle between a lamination surface of an elastic pressing head in a second embodiment of a microneedle patch base layer lamination device of the present disclosure and a horizontal direction is 13°.
Figure 45:
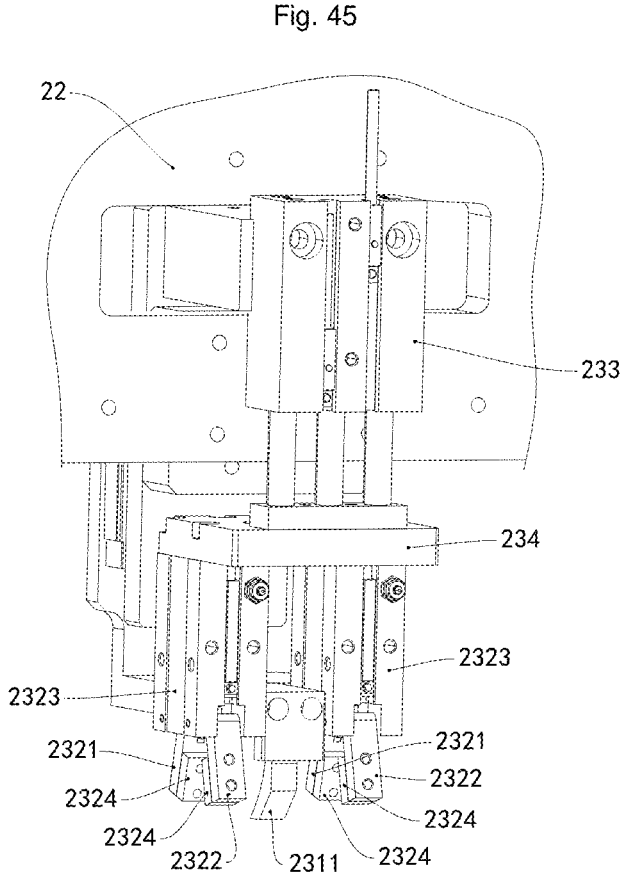
FIG. 45 is a structural diagram of a demolding and separation apparatus in a first embodiment of a microneedle patch demolding and separation device of the present disclosure from a second perspective.
Figure 46:
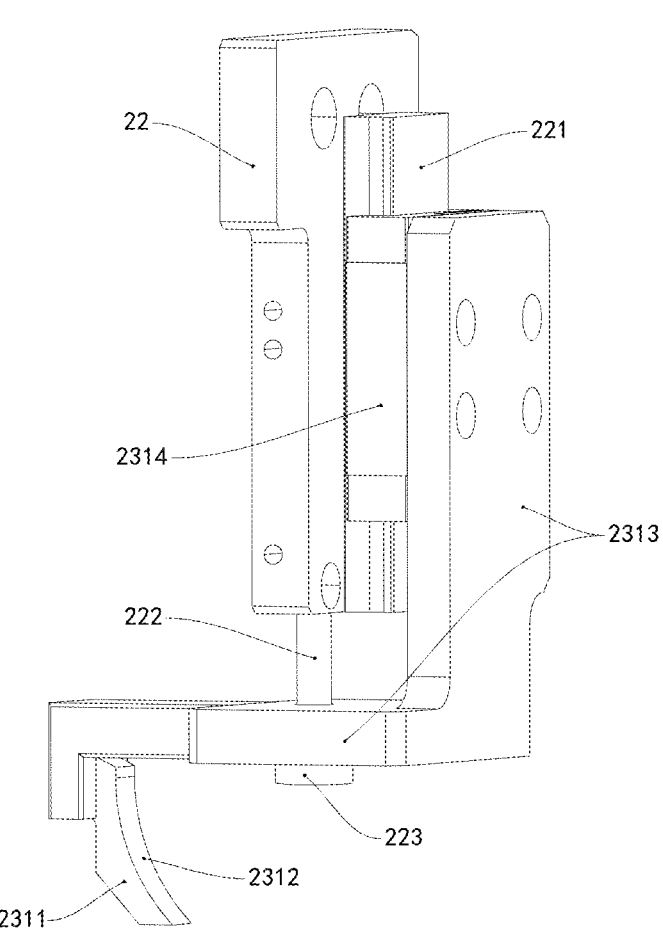
FIG. 46 is a partial structural diagram of a demolding and separation apparatus in a first embodiment of a microneedle patch demolding and separation device of the present disclosure.

Referring to FIG. 37 to FIG. 40, FIG. 37 is a lamination effect diagram when an inclination angle $\beta$ between lamination surfaces 9311 and 9311' of elastic pressing heads 931 and 931' and a horizontal direction is 1°, FIG. 38 is a lamination effect diagram when an inclination angle $\beta$ between lamination surfaces 9311 and 9311' of elastic pressing heads 931 and 931' and a horizontal direction is 5°, FIG. 39 is a lamination effect diagram when an inclination angle $\beta$ between lamination surfaces 9311 and 9311' of elastic pressing heads 931 and 931' and a horizontal direction is 9°, and FIG. 40 is a lamination effect diagram when an inclination angle $\beta$ between lamination surfaces 9311 and 9311' of elastic pressing heads 931 and 931' and a horizontal direction is 13°. It can be seen from the lamination effect diagrams of FIG. 37 to FIG. 40 that the lamination surfaces 9311 and 9311' of the elastic pressing heads 931 and 931' are inclined relative to the horizontal direction, which can effectively and completely discharge the gas between the adhesive layer 12 and the base layer 13 of the microneedle patch, thereby avoiding the possibility of bubbles between the adhesive layer 12 and the base layer 13 of the microneedle patch, ensuring that defective products cannot be caused by the existence of bubbles between the microneedle patch and the adhesive layer 12, then improving the yield rate, and enhancing the adhesion stability between the microneedle patch and the support plate 11, so that the microneedle patch can be firmly supported by the support plate 11.

In the microneedle patch base layer lamination device 9 of the present disclosure, the lamination apparatus 93 may also be fixedly arranged on the rack 95, and the carrier 100 is movable in the horizontal direction and the vertical direction. When performing the lamination operation on the product to be laminated, the carrier 100 is controlled to move to below the elastic pressing heads 936, 937, 931 and 931', and the carrier 100 is controlled to rise, so that the elastic pressing heads 936, 937, 931 and 931' are laminated on the product to be laminated, thereby achieving adhesion of the adhesive layer 12 and the base layer 13 of the microneedle, so that the microneedle patch is firmly supported by the support plate 11.

First embodiment of microneedle patch demolding and separation device:

Referring to FIG. 41 to FIG. 46, the embodiment discloses a microneedle patch demolding and separation device, including a rack 25, a movement control mechanism 21, a movable seat 22, and a demolding and separation apparatus 23. The demolding and separation apparatus 23 is arranged on the movable seat 22, a carrier 3 is supported on the rack 25, the movement control mechanism 21 is arranged on the rack 25 and is able to control the movable seat 22 and/or the carrier 3 to move in a vertical direction and a horizontal direction respectively, and the carrier 6 is configured to place a mold 28 (referring to FIG. 47) filled and cured to form a microneedle patch. The demolding and separation apparatus 23 in the embodiment may be located above the carrier 3 in the vertical direction, and the demolding and separation apparatus 23 includes a clamping part 232 and a separation part 231. The separation part 231 may be movably supported on the movable seat 22 in the vertical direction, and the separation part 231 may protrude out of the clamping part 232 toward the carrier 3 in the vertical direction. In addition, the separation part 231 in the embodiment is configured to force a stripping end of the microneedle patch on the carrier 3 to be demolded, and the clamping part 232 is configured to clamp the stripping end of the microneedle patch.

The microneedle patch formed by a mold 28 includes a base layer 13 and a microneedle array 14 composed of a plurality of microneedles arranged on the base layer 13, thereby forming a first product to be demolded on the carrier 3 of the microneedle patch demolding and separation device in the embodiment. After the microneedle patch formed in the mold 28 is dried, cured and formed, a support plate 11 adhered with an adhesive layer 12 may be placed on the mold 28. Since the support plate 11 is provided with an accommodating hole 111 corresponding to the microneedle array 14 in a penetrating manner, the support plate 11 is located between the adhesive layer 12 and the base layer 13, a part of the adhesive layer 12 is adhered to a side surface, away from the base layer 13, of the support plate 11, the other part of the adhesive layer 12 covers the accommodating hole 111, and then the adhesive layer 12 corresponding to the accommodating hole 111 of the support plate 11 is laminated and adhered to the base layer 13, so that the microneedle patch is supported by the support plate 11, thereby forming a second product to be demolded on the carrier 3 of the microneedle patch demolding and separation device in the embodiment.

In the process of performing a product demolding operation by the microneedle patch demolding and separation device in the embodiment, the movement control mechanism 21 of the microneedle patch demolding and separation device in the embodiment controls the movable seat 22 and/or the carrier 3 to move in the vertical direction and the horizontal direction respectively. Since the demolding and separation apparatus 23 is arranged on the movable seat 22, the demolding and separation apparatus 23 is located above the mold 28 placed on the carrier 3 in the vertical direction, that is, the demolding and separation apparatus 23 is located above the first product to be demolded or the second product to be demolded formed in the carrier 3 in the vertical direction. Then, the movement control mechanism 21 controls the movable seat 22 and/or the carrier 3 to move in the vertical direction, so that the demolding and separation apparatus 23 approaches the mold 28 placed on the carrier 3 in the vertical direction. Since the separation part 231 of the demolding and separation apparatus 23 may protrude out of the clamping part 232 toward the carrier 3 in the vertical direction, the separation part 231 is pressed against the mold 28 or the microneedle patch. At this time, the clamping part 232 of the demolding and separation apparatus 23 is not in contact with the mold 28 or the product to be demolded, and at the same time, since the separation part 231 may be movably supported on the movable seat 22 in the vertical direction, the separation part 231 moves away from the mold 28 in the vertical direction when subjected to the pressing reaction force, and automatically rebounds for buffering, thereby avoiding defective products caused by the damage of the separation part 231 to the mold 28 or the product to be demolded.

Then, the movement control mechanism 21 controls the movable seat 22 and/or the carrier 3 to move in the horizontal direction or the vertical direction, so that the separation part 231 forces the stripping end of the microneedle patch to be demolded from the mold 28, that is, the separation part 231 forces the stripping end of the base layer 13 of the first product to be demolded to be demolded from the mold 28, or the separation part 231 forces the stripping end of the support plate 11 of the second product to be demolded to be demolded from the mold 28, and then controls the clamping part 232 to clamp the stripping end of the microneedle patch, that is, the clamping part 232 clamps the stripping end of the base layer 13 of the first product to be demolded, or the clamping part 232 clamps the stripping end of the support plate 11 of the second product to be demolded. Then, the movement control mechanism 21 controls the movable seat 22 and/or the carrier 3 to move in the vertical direction and the horizontal direction. Since the separation part 231 may be movably supported on the movable seat 22 in the vertical direction, the separation part 231 moves away from the stripping end of the microneedle patch and protrudes out of the clamping part 232 in the vertical direction, which can avoid the separation part 231 from causing interference when the clamping part 232 clamps the stripping end of the microneedle patch to perform the demolding operation. As the clamping part 232 clamps the stripping end of the microneedle patch and moves in the vertical direction and the horizontal direction, the microneedle patch is demolded from the mold 28 at an angle relative to the horizontal direction, that is, the first product to be demolded is demolded from the mold 28 at an angle relative to the horizontal direction, or the second product to be demolded is demolded from the mold 28 at an angle relative to the horizontal direction, so that the microneedle array 14 approaches the stripping end of the microneedle patch and is demolded from a micro-hole cavity row by row, and the resistance encountered in the demolding process of the microneedle patch is reduced, thereby automatically completing the demolding operation of the microneedle patch product, with a high degree of automation. In the process of performing the demolding operation, the separation part 231 is separated from the stripping end of the microneedle patch and protrudes out of the clamping part 232 in the vertical direction and moves, which can avoid the separation part 231 from causing interference when the clamping part 232 clamps the stripping end of the microneedle patch to perform the demolding operation, thereby effectively ensuring the operational stability and reliability of the demolding operation.

Compared with an existing method that requires a relatively large adsorption force to demold the microneedle patch from the mold 28 in the vertical direction to cause deformation, resulting in defective products, the microneedle patch demolding and separation device in the embodiment controls the microneedle patch to be smoothly demolded from the mold 28 at an angle relative to the horizontal direction by lifting, which reduces the action force and resistance borne by the microneedle patch in the demolding process, and can effectively avoid the damage and breakage of a microneedle due to deformation of the microneedle patch in the demolding process, thereby improving the yield rate, and the degree of automation is high, and the demolding operation is stable and reliable, thereby improving the production efficiency and reducing the production cost.

In order to improve the smoothness of the movement of the separation part 231 relative to the movable seat 22 in the vertical direction, and the operational reliability and stability, the movable seat 22 in the embodiment is provided with a first slide bar 222 extending in the vertical direction, a linkage seat 2313 of the separation part 231 is slidably sleeved on the first slide bar 222, and a bottom end of the first slide bar 222 is provided with a first limit plate 223. The first limit plate 223 is located on the side, close to the carrier 3, of the linkage seat 2313 in the vertical direction, and the movable seat 22 is provided with a slide rail 221 extending along the vertical direction, the linkage seat 2313 of the separation part 231 is provided with a slide seat 2314, and the slide seat 2314 is slidably matched with the slide rail 221.

In some embodiments, the separation part 231 in the embodiment is a hook shovel 2311, a hook-off end of the hook shovel 2311 is configured to force the stripping end of the microneedle patch to be demolded, and a hook-off surface 2312, connected to the hook-off end of the hook shovel 2311, of the hook shovel 2311 is configured to support the stripping end of the microneedle patch. In some embodiments, the hook-off surface 2312 of the hook shovel 2311 extends in an arc shape in the vertical direction. In addition, the demolding and separation apparatus 23 in the embodiment further includes a clamping control mechanism. The clamping control mechanism is arranged on the movable seat 22 and may control the clamping part 232 to move in the vertical direction. The clamping part 232 in the embodiment includes a first clamping jaw 2321, a second clamping jaw 2322, and a clamping jaw control mechanism. The clamping jaw control mechanism may control the first clamping jaw 2321 and the second clamping jaw 2322 to move toward or away from each other in the horizontal direction. In order to avoid the damage to the product in the clamping process and ensure the yield rate of the product, the clamping part 232 in the embodiment further includes two elastic pads 2324. One elastic pad 2324 is arranged on a first clamping surface, close to the second clamping jaw 2322, of the first clamping jaw 2321 in the horizontal direction, and the other elastic pad 2324 is arranged on a second clamping surface, close to the first clamping jaw 2321, of the second clamping jaw 2322 in the horizontal direction. In some embodiments, the number of clamping parts 232 in the embodiment is two, and the two clamping parts 232 are respectively located on both sides of the separation part 231 in the horizontal direction, that is, the two clamping parts 232 are respectively located on both sides of the hook shovel 2311 in the horizontal direction, and the clamping control mechanism may control the two clamping parts 232 to move synchronously in the vertical direction. The clamping control mechanism in the embodiment is a clamping cylinder 233, and the clamping claw control mechanism in the embodiment is a clamping claw cylinder 2323. The clamping claw cylinder 2323 is arranged on a connecting plate 234, and the clamping cylinder 233 may control the connecting plate 234 to move in the vertical direction, thereby controlling the clamping claw cylinder 2323, the first clamping claw 2321, and the second clamping claw 2322 to move in the vertical direction. In addition, the elastic pad 2324 in the embodiment is made of a silica gel material, which has good flexibility, good surface gloss, does not damage the product surface, and is good in chemical stability, environmentally friendly and non-toxic, so that the first clamping claw 2321 and the second clamping claw 2322 do not damage the product when clamping the product.

Figure 47:
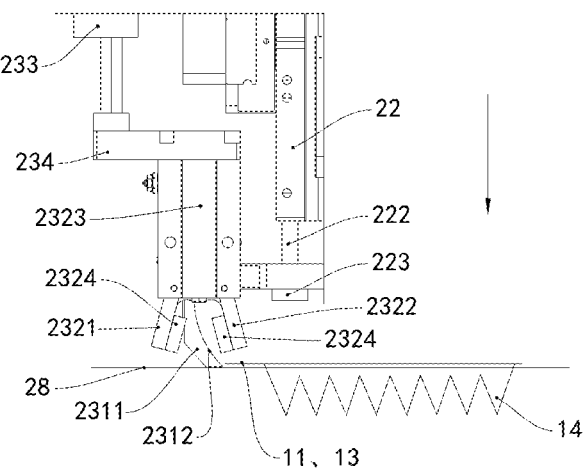
FIG. 47 is a schematic diagram of a first operating state of a first embodiment of a microneedle patch demolding and separation device of the present disclosure.

Referring to FIG. 47, in the process of performing the product demolding operation, the movement control mechanism 21 of the microneedle patch demolding and separation device in the embodiment controls the movable seat 22 and/or the carrier 3 to move in the vertical direction and the horizontal direction respectively. Since the demolding and separation apparatus 23 is arranged on the movable seat 22, the demolding and separation apparatus 23 is located above the microneedle patch placed on the carrier 3 in the vertical direction, that is, the demolding and separation apparatus 23 is located above the first product to be demolded or the second product to be demolded placed on the carrier 3 in the vertical direction. Then, the movement control mechanism 21 controls the movable seat 22 and/or the carrier 3 to move downward in the vertical direction, so that the demolding and separation apparatus 23 approaches the mold 28 placed on the carrier 3 in the vertical direction. Since the separation part 231 is only subjected to its own gravity in the vertical direction, the separation part 231 of the demolding and separation apparatus 23 may protrude out of the clamping part 232 toward the carrier 3 under its own gravity in the vertical direction, and the separation part 231 is pressed against the mold 28 placed on the carrier 3, that is, the hook-off end of the hook shovel 2311 is pressed against the mold 28 placed on the carrier 3. At this time, the first clamping jaw 2321 and the second clamping jaw 2322 are not in contact with the mold 28 or the product to be demolded, and at the same time, since the hook shovel 2311 may be movably supported on the movable seat 22 in the vertical direction, the hook-off end of the hook shovel 2311 may move away from the mold 28 in the vertical direction when subjected to the pressing reaction force of the mold 28, and automatically rebounds for buffering. The mass of the separation part 231 is relatively small, when the separation part 231 is pressed against the mold 28 or the surface of the product to be demolded, the action force on the surface of the mold 28 or the product to be demolded is relatively small. Moreover, the separation part 231 is made of a non-hard material, even if the hook shovel 2311 (separation part 231) is frequently laminated on the surface of the mold 28 or the product to be demolded for a long time, the defective products caused by the damage of the hook-off end of the hook shovel 2311 to the mold 28 or the product to be demolded may also be avoided.

Figures 48, 49:
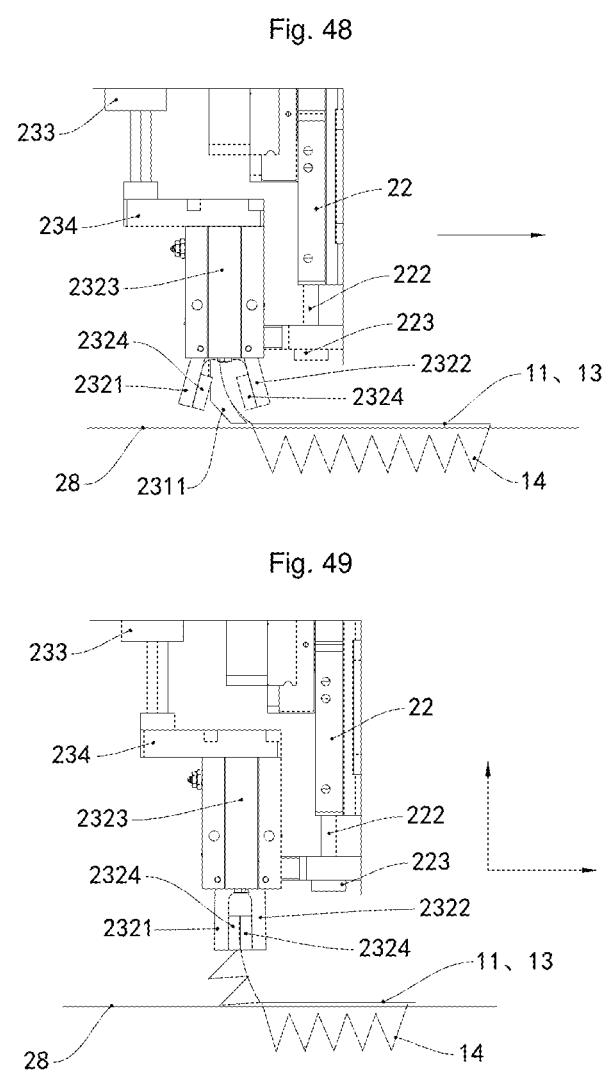

Referring to FIG. 48, the movement control mechanism 21 controls the movable seat 22 and/or the carrier 3 to move in the horizontal direction, so that the hook-off end of the hook shovel 2311 forces the stripping end of the microneedle patch to be demolded from the mold 28, that is, the hook-off end of the hook shovel 2311 forces the stripping end of the base layer 13 of the first product to be demolded or the stripping end of the support plate 11 of the second product to be demolded to be demolded from the mold 28, and the stripping end of the microneedle patch is supported on the hook-off surface 2312 of the hook shovel 2311, so as to ensure that the stripping end of the microneedle patch can enter the action range of the opened first clamping jaw 2321 and the second clamping jaw 2322 within 8 to 10 mm. If the distance is less than 8 mm, the first clamping jaw 2321 and the second clamping jaw 2322 cannot be better stressed to clamp the stripping end of the microneedle patch to ensure the demolding of the microneedle patch. If the distance is greater than 10 mm, the microneedle of the microneedle patch may be damaged.

Then, the clamping control mechanism controls the clamping part 232 to move toward the mold 28 in the vertical direction, so that the clamping part 232 is located at a predetermined clamping position, and the clamping jaw control mechanism of the clamping part 232 controls the first clamping jaw 2321 and the second clamping jaw 2322 to move toward each other in the horizontal direction, so that the two elastic pads 2324 clamp the stripping end of the microneedle patch, that is, the elastic pad 2324 on the first clamping jaw 2321 and the elastic pad 2324 on the second clamping jaw 2322 clamp the stripping end of the base layer 13 of the first product to be demolded or the stripping end of the support plate 11 of the second product to be demolded. Then, the clamping control mechanism controls the clamping part 232 to move away from the mold 28 in the vertical direction to reset, so that the stripping end of the microneedle patch is separated from the hook-off surface 2312 of the hook shovel 2311 and inclined relative to the horizontal direction.

Referring to FIG. 49, the movement control mechanism 21 controls the movable seat 22 and/or the carrier 3 to move in the vertical direction and the horizontal direction. Since the separation part 231 may be movably supported on the movable seat 22 in the vertical direction, the hook shovel 2311 moves away from the stripping end of the microneedle patch under the action of its own gravity, and protrudes out of the clamping part 232 in the vertical direction to reset, which can avoid the hook shovel 2311 from causing interference when the elastic pad 2324 on the first clamping jaw 2321 and the elastic pad 2324 on the second clamping jaw 2322 clamp the stripping end of the microneedle patch to perform the demolding operation. As the elastic pad 2324 on the first clamping jaw 2321 and the elastic pad 2324 on the second clamping jaw 2322 clamp the stripping end of the microneedle patch to move in the vertical direction and the horizontal direction, the microneedle patch is demolded from the mold 28 at an angle relative to the horizontal direction, that is, the first product to be demolded is demolded from the mold 28 at an angle relative to the horizontal direction, or the second product to be demolded is demolded from the mold 28 at an angle relative to the horizontal direction, thereby automatically completing the demolding operation of the microneedle patch product. In some embodiments, in the process of demolding the microneedle patch from the mold 28 at an angle relative to the horizontal direction, an inclination angle $\alpha$ between the microneedle patch and the horizontal direction is between 43° and 68°. When $43°\leq\alpha\leq68°$, and the microneedle patch is demolded, the microneedle patch moves in the horizontal direction while the lifting height in the vertical direction just meets the demolding height of the microneedle array 14, so that the microneedle array 14 may be smoothly demolded from the micro-hole cavity of the mold 28, thereby ensuring the yield rate of the product. When $\alpha<43°$, and the microneedle patch is demolded, the microneedle patch moves in the horizontal direction while the lifting height in the vertical direction is less than the demolding height of the microneedle array 14, so that a tip of the microneedle array 14 is still located in the micro-hole cavity of the mold 28, resulting in the breakage of the tip of the microneedle array 14 and defective products. When $\alpha>68°$, and the microneedle patch is demolded, the microneedle patch moves in the horizontal direction while the lifting height in the vertical direction is greater than the demolding height of the microneedle array 14, so that when the front row of microneedle arrays 14 are released from the mold 28, the rear row of microneedle arrays 14 may be driven to touch a side wall of the micro-hole cavity of the mold 28, resulting in breakage and defective products.

In order to further improve the operational stability and reliability of the microneedle patch demolding and separation device in the embodiment to ensure the production quality of the product, the movement control mechanism 21 in the embodiment includes a first motor 211, a first screw rod 2117, a first sliding table 212, a second motor 215, a second screw rod (not shown), a second sliding table 216, a third motor 219, and a third screw rod. The first motor 211 and the first screw rod 2117 are respectively arranged on the rack 25, a driving shaft of the first motor 211 is connected to the first screw rod 2117, the first screw rod 2117 extends in a first direction, the first sliding table 212 may be slidably sleeved on the first screw rod 2117 in the first direction, the second motor 215 and the second screw rod are respectively arranged on the first sliding table 212, a driving shaft of the second motor 215 is connected to the second screw rod, the second screw rod extends in a second direction, the second sliding table 216 may be slidably sleeved on the second screw rod in the second direction, the second direction and the first direction intersect in the horizontal direction, the third motor 219 and the third screw rod are respectively arranged on the second sliding table 216, a driving shaft of the third motor 219 is connected to the third screw rod, the third screw rod extends in the vertical direction, and the movable seat 22 may be slidably sleeved on the third screw rod in the vertical direction. The movement control mechanism 21 in the embodiment forms a servo control mechanism through the cooperation of the motors, the screw rods, and the sliding tables, which can ensure that the microneedle patch demolding and separation device in the embodiment cannot cause the movable seat 22 to drive the demolding and separation apparatus 23 to shake or move inaccurately in the operation process due to the excessive driving speed of the movement control mechanism 21 or under the action of an external force, thereby ensuring the production quality of the product, and then improving the operational stability and reliability of the microneedle patch demolding and separation device in the embodiment. In the embodiment, the vertical direction is a Z-axis direction, the first direction is an X-axis direction, and the second direction is a Y-axis direction.

In order to further improve the operational stability and reliability of the microneedle patch demolding and separation device in the embodiment to ensure the production quality of the product, in the embodiment, the rack 25 is provided with a first guide rail 214, the first guide rail 214 extends in the first direction, the first sliding table 212 is provided with a first slide block 2116, and the first slide block 2116 may be slidably matched with the first guide rail 214 in the first direction. The first sliding table 212 is provided with a second guide rail 2113, the second guide rail 2113 extends in the second direction, the second sliding table 216 is provided with a second slide block (not shown), and the second slide block may be slidably matched with the second guide rail 2113 in the second direction. The second sliding table 216 is provided with a third guide rail 2110, the third guide rail 2110 extends in the vertical direction, the movable seat 22 is provided with a third slide block 2111, and the third slide block 2111 may be slidably matched with the third guide rail 2110 in the vertical direction. Specifically, in the embodiment, the rack 25 is provided with two first photoelectric sensors 213, the two first photoelectric sensors 213 are arranged side by side in the first direction, each first photoelectric sensor 213 is provided with a first through groove, the first sliding table 212 is provided with a first sensing piece 2112, the first sensing piece 2112 may be movably inserted into the first through groove of each first photoelectric sensor 213 in the first direction, and the two first photoelectric sensors 213 are respectively configured as a stop point at which the first sensing piece 2112 reciprocates in the first direction. Specifically, in the embodiment, the first sliding table 212 is provided with two second photoelectric sensors 217, the two second photoelectric sensors 217 are arranged side by side in the second direction, each second photoelectric sensor 217 is provided with a second through groove, the second sliding table 216 is provided with a second sensing piece 218, the second sensing piece 218 may be movably inserted into the second through groove of each second photoelectric sensor 217 in the second direction, and the two second photoelectric sensors 217 are respectively configured as a stop point at which the second sensing piece 218 reciprocates in the second direction. Specifically, in the embodiment, the second sliding table 216 is provided with two third photoelectric sensors, the two third photoelectric sensors are arranged side by side in the vertical direction, each third photoelectric sensor is provided with a third through groove, the movable seat 22 is provided with a third sensing piece, the third sensing piece may be movably inserted into the third through groove of each third photoelectric sensor in the vertical direction, and the two third photoelectric sensors are respectively configured as a stop point at which the first sensing piece reciprocates in the vertical direction.

In order to further improve the degree of automation of the microneedle patch demolding and separation device in the embodiment, the movement control mechanism 21 in the embodiment further includes a conveying apparatus 24 arranged on the rack 25. The conveying apparatus 24 includes a first conveyor belt 241, a second conveyor belt 242, and a conveying control mechanism. The first conveyor belt 241 and the second conveyor belt 242 may be movably supported on the rack 25, and the conveying control mechanism may control the first conveyor belt 241 and the second conveyor belt 242 to move synchronously in the horizontal direction, and the carrier 3 is placed on the first conveyor belt 241 and the second conveyor belt 242, so that the conveying control mechanism controls the first conveyor belt 241 and the second conveyor belt 242 to move synchronously in the horizontal direction to automatically convey the carrier 3, thereby improving the operation efficiency. Specifically, the conveying control mechanism in the embodiment includes a fourth motor 243, a driving wheel, a driven wheel, a synchronous belt, a linkage shaft 244, a first rotating wheel, a second rotating wheel, a third rotating wheel 245, and a fourth rotating wheel 246. The fourth motor 243 is arranged on the rack 25, the first rotating wheel, the second rotating wheel, the third rotating wheel 245, and the fourth rotating wheel 246 are respectively rotatably supported on the rack 25, the driving wheel is sleeved on a driving shaft of the fourth motor 243, the driven wheel is sleeved on the linkage shaft 244, the synchronous belt is sleeved between the driving wheel and the driven wheel, and the first rotating wheel and the second rotating wheel are respectively rotatably supported on the linkage shaft 244. The third rotating wheel 245 and the first rotating wheel are arranged side by side in a moving direction of the first conveyor belt 241, the first conveyor belt 241 is sleeved between the third rotating wheel 245 and the first rotating wheel, the fourth rotating wheel 246 and the second rotating wheel are arranged side by side in the moving direction of the first conveyor belt 241, and the second conveyor belt 242 is sleeved between the fourth rotating wheel 246 and the second rotating wheel, so that the conveying control mechanism in the embodiment can control the first conveyor belt 241 and the second conveyor belt 242 to move synchronously in the horizontal direction stably and reliably. Specifically, the conveying control mechanism in the embodiment may control the first conveyor belt 241 and the second conveyor belt 242 to move synchronously in the X-axis direction.

The number of demolding and separation apparatuses 23 in the microneedle patch demolding and separation device in the embodiment is at least two, and the demolding and separation apparatuses 23 can be controlled to move in the horizontal direction by a cylinder or a servo, so as to adjust a distance between the two adjacent demolding and separation apparatuses 23, so that the plurality of microneedle patches can perform the demolding operation simultaneously, thereby greatly improving the production efficiency and reducing the production cost.

Second embodiment of microneedle patch demolding and separation device:

As an illustration of a second embodiment of the microneedle patch demolding and separation device of the present disclosure, only the differences from the first embodiment of the microneedle patch demolding and separation device are described below.

Figures 50, 51:
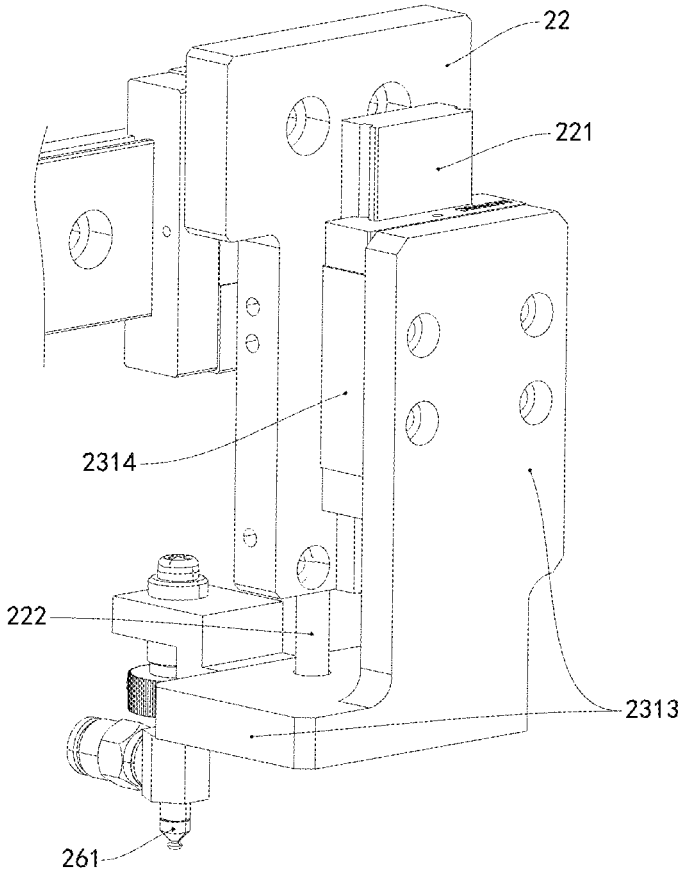
FIG. 50 is a front view of a demolding and separation apparatus in a second embodiment of a microneedle patch demolding and separation device of the present disclosure.
FIG. 51 is a partial structural diagram of a demolding and separation apparatus in a second embodiment of a microneedle patch demolding and separation device of the present disclosure.

Referring to FIG. 50 and FIG. 51, the separation part 231 of the demolding and separation apparatus 26 in the embodiment is a vacuum suction cup 261, and the vacuum suction cup 261 can absorb the stripping end of the microneedle patch to force the stripping end of the microneedle patch to be demolded.

Figures 52, 53:
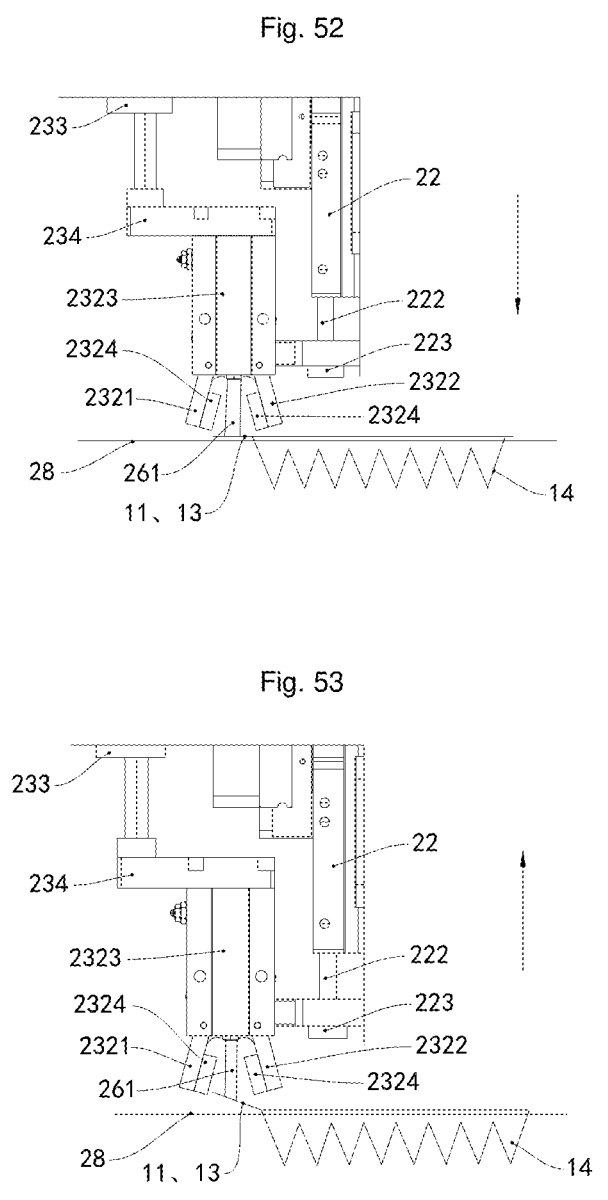

Referring to FIG. 52, in the process of performing the product demolding operation, since the separation part 231 in the embodiment is the vacuum suction cup 261, under a control operation of the movement control mechanism 21, an absorption end of the vacuum suction cup 261 can be pressed against the stripping end of the microneedle patch on the mold 28. At this time, the first clamping jaw 2321 and the second clamping jaw 2322 are not in contact with the mold 28 or the product to be demolded. At the same time, since the vacuum suction cup 261 may be movably supported on the movable seat 22 in the vertical direction, the vacuum suction cup 261 naturally sags under its own gravity and is pressed against the surface of the mold 28. The absorption end of the vacuum suction cup 261 may force the vacuum suction cup 261 to move away from the mold 28 in the vertical direction when subjected to the pressing reaction force, and automatically rebounds for buffering. The mass of the vacuum suction cup 261 is relatively small, and the pressure on the surface of the mold 28 or the microneedle patch is always the gravity borne by the vacuum suction cup 261, thereby avoiding defective products caused by the damage of the absorption end of the vacuum suction cup 261 to the mold 28 or the product to be demolded.

Referring to FIG. 53, the movement control mechanism 21 controls the movable seat 22 and/or the carrier 3 to move in the vertical direction, so that the vacuum suction cup 261 adsorbs the stripping end of the microneedle patch to move in the vertical direction, so as to force the stripping end of the microneedle patch to be demolded from the mold 28, that is, the vacuum suction cup 261 adsorbs the stripping end of the base layer 13 of the first product to be demolded to be demolded from the mold 28, or, the vacuum suction cup 261 adsorbs the stripping end of the support plate 11 of a second product to be demolded to be demolded from the mold 28, so as to ensure that the stripping end of the microneedle patch can enter the action range of the opened first clamping jaw 2321 and the second clamping jaw 2322. Since the demolding area of the stripping end of the microneedle patch is relatively small, the vacuum suction cup 261 may separate the stripping end of the microneedle patch from the mold 28 only by a relatively small adsorption force, so that defective products caused by deformation of the microneedle patch can be effectively avoided.

Then, the clamping control mechanism controls the clamping part 232 to move toward the mold 28 in the vertical direction, so that the clamping part 232 is located at a predetermined clamping position, and the clamping jaw control mechanism controls the first clamping jaw 2321 and the second clamping jaw 2322 to move toward each other in the horizontal direction, so that the two elastic pads 2324 clamp the stripping end of the microneedle patch, that is, the elastic pad 2324 on the first clamping jaw 2321 and the elastic pad 2324 on the second clamping jaw 2322 clamp the stripping end of the base layer 13 of the first product to be demolded, or, the elastic pad 2324 on the first clamping jaw 2321 and the elastic pad 2324 on the second clamping jaw 2322 clamp the stripping end of the support plate 11 of the second product to be demolded. Then, the vacuum suction cup 261 is closed, and the clamping control mechanism controls the clamping part 232 to move away from the mold 28 in the vertical direction to reset, so that the stripping end of the microneedle patch is inclined relative to the horizontal direction.

Figures 54, 55:
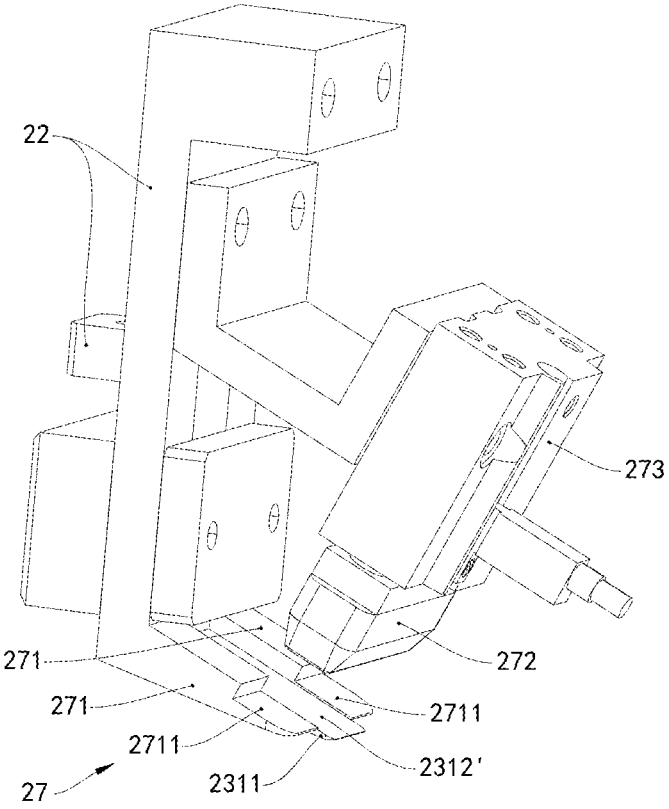
FIG. 54 is a schematic diagram of a third operating state of a second embodiment of a microneedle patch demolding and separation device of the present disclosure.
FIG. 55 is a structural diagram of a demolding and separation apparatus in a third embodiment of a microneedle patch demolding and separation device of the present disclosure.

Referring to FIG. 54, the movement control mechanism 21 controls the movable seat 22 and/or the carrier 3 to move in the vertical direction and the horizontal direction. The vacuum suction cup 261 may be movably supported on the movable seat 22 in the vertical direction, thereby avoiding the absorption end of the vacuum suction cup 261 from having the excessive external thrust on the stripping end of the microneedle patch and affecting the elastic pad 2324 on the first clamping jaw 2321 and the elastic pad 2324 on the second clamping jaw 2322 to clamp the stripping end of the microneedle patch to perform the demolding operation, and effectively ensuring the operational stability and reliability of the demolding operation. As the elastic pad 2324 on the first clamping jaw 2321 and the elastic pad 2324 on the second clamping jaw 2322 clamp the stripping end of the microneedle patch to move in the vertical direction and the horizontal direction, the microneedle patch is demolded from the mold 28 at an angle relative to the horizontal direction, that is, the first product to be demolded is demolded from the mold 28 at an angle relative to the horizontal direction, or the second product to be demolded is demolded from the mold 28 at an angle relative to the horizontal direction, thereby automatically completing the demolding operation of the microneedle patch product.

Third embodiment of microneedle patch demolding and separation device:

As an illustration of a third embodiment of the microneedle patch demolding and separation device of the present disclosure, only the differences from the first embodiment of the microneedle patch demolding and separation device are described below.

Referring to FIG. 55, the separation part 231 of the demolding and separation apparatus 27 in the embodiment is a hook shovel 2311, and a hook-off surface 2312' of the hook shovel 2311 is inclined relative to the horizontal direction. The clamping part of the demolding and separation apparatus 27 in the embodiment includes a sliding shovel 271, a pressing block 272, and a pressing control mechanism. The sliding shovel 271 is located on a side of the hook shovel 2311 in the horizontal direction, the pressing block 272 is located above the sliding shovel 271 in the vertical direction, the pressing control mechanism may control the pressing block 272 to move toward or away from the sliding shovel 271, and the pressing block 272 may be pressed against a support surface 2711 of the sliding shovel 271. The support surface 2711 of the sliding shovel 271 is configured to support the stripping end of the microneedle patch. Specifically, the support surface 2711 of the sliding shovel 271 in the embodiment is inclined relative to the horizontal direction, and the moving direction of the pressing block 272 is perpendicular to the support surface 2711 of the sliding shovel 271. In some embodiments, the hook-off surface 2312' of the hook shovel 2311 and the support surface 2711 of the sliding shovel 271 have the same inclination direction and inclination angle, that is, the hook-off surface 2312' of the hook shovel 2311 and the support surface 2711 of the sliding shovel 271 are arranged parallel to each other.

The hook shovel 2311 in the embodiment is provided with a second slide bar 274 extending in the vertical direction, a top end of the second slide bar 274 slidably penetrates through the movable seat 22, and the top end of the second slide bar 274 is provided with a second limit plate 275. The second limit plate 275 is located on the side, away from the carrier 3, of the movable seat 22 in the vertical direction, which ensures that the hook shovel 2311 may be stably and reliably supported on the movable seat 22 in the vertical direction, so that the structure of the demolding and separation apparatus 27 is simple and compact. In order to further ensure the stability and reliability of the clamping operation, the number of sliding shovels 271 in the embodiment is two, and the two sliding shovels 271 are respectively located on both sides of the hook shovel 2311 in the horizontal direction, and the clamping block 272 may be pressed against the support surfaces 2711 of the two sliding shovels 271 synchronously. In addition, the clamping control mechanism in the embodiment is a clamping cylinder 273.

Figures 56, 57:
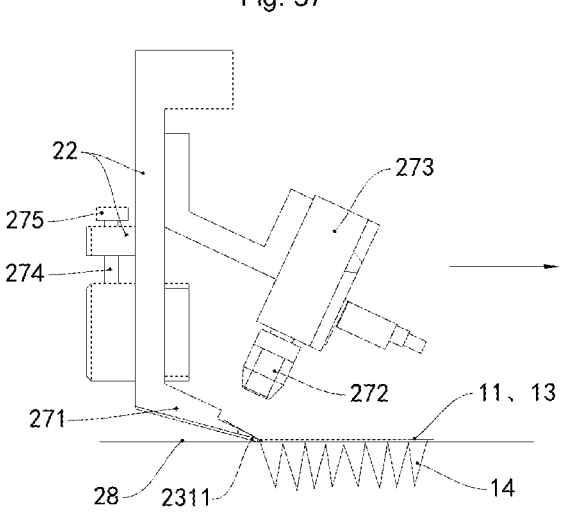
FIG. 56 is a schematic diagram of a first operating state of a third embodiment of a microneedle patch demolding and separation device of the present disclosure.
FIG. 57 is a schematic diagram of a second operating state of a third embodiment of a microneedle patch demolding and separation device of the present disclosure.

Referring to FIG. 56, in the process of performing the product demolding operation, under the control operation of the movement control mechanism 21, the separation part 231 is pressed against the mold 28 placed on the carrier 3, that is, the hook-off end of the hook shovel 2311 is pressed against the mold 28 placed on the carrier 3. At this time, the sliding shovel 271 is not in contact with the mold 28 or the product to be demolded. At the same time, since the hook shovel 2311 may be movably supported on the movable seat 22 in the vertical direction, the hook-off end of the hook shovel 2311 may move away from the mold 28 in the vertical direction when subjected to the pressing reaction force of the mold 28, and automatically rebounds for buffering, thereby avoiding the problem of defective products caused by the damage of the hook-off end of the hook shovel 2311 to the mold 28 or the product to be demolded.

Referring to FIG. 57, the movement control mechanism 21 controls the movable seat 22 and/or the carrier 3 to move in the horizontal direction, so that the hook-off end of the hook shovel 2311 forces the stripping end of the microneedle patch to be demolded from the mold 28, that is, the hook-off end of the hook shovel 2311 forces the stripping end of the base layer 13 of the first product to be demolded to be demolded from the mold 28, or, the hook-off end of the hook shovel 2311 forces the stripping end of the support plate 11 of the second product to be demolded to be demolded from the mold 28, the stripping end of the microneedle patch is supported on the hook-off surface 2312' of the hook shovel 2311, and at the same time, stripping end of the microneedle patch is supported on the support surface 2711 of the sliding shovel 271.

Then, the clamping control mechanism controls the clamping block 272 to move toward the sliding shovel 271 to clamp the stripping end of the microneedle patch, that is, the pressing block 272 and the support surface 2711 of the sliding shovel 271 clamp the stripping end of the base layer 13 of the first product to be demolded, or, the pressing block 272 and the support surface 2711 of the sliding shovel 271 clamp the stripping end of the support plate 11 of the second product to be demolded, so that the force of clamping the stripping end of the microneedle patch is more stable, thereby ensuring the yield rate of the product.

Figure 58:
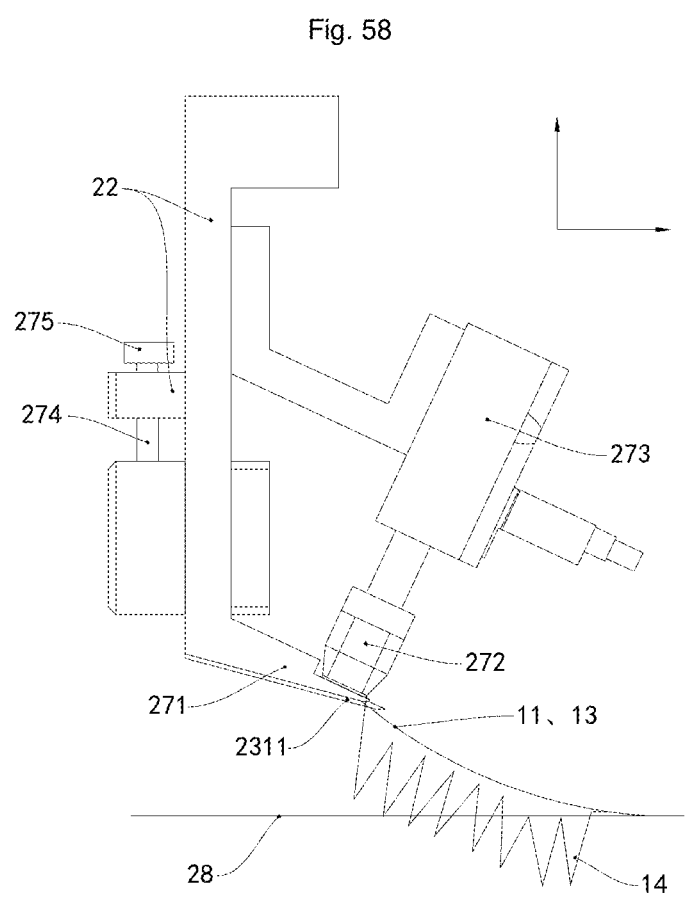

Referring to FIG. 58, the movement control mechanism 21 controls the movable seat 22 and/or the carrier 3 to move in the vertical direction and the horizontal direction. Since the separation part 231 may be movably supported on the movable seat 22 in the vertical direction, the hook shovel 2311 moves away from the stripping end of the microneedle patch under its own gravity and protrudes out of the sliding shovel 271 in the vertical direction to reset, which can avoid the hook shovel 2311 from causing interference when the pressing block 272 and the support surface 2711 of the sliding shovel 272 clamp the stripping end of the microneedle patch to perform the demolding operation. As the pressing block 272 and the support surface 2711 of the sliding shovel 271 clamp the stripping end of the microneedle patch to move in the vertical direction and horizontal direction, the microneedle patch is demolded from the mold 28 at an angle relative to the horizontal direction, that is, the first product to be demolded is demolded from the mold 28 at an angle relative to the horizontal direction, or the second product to be demolded is demolded from the mold 28 at an angle relative to the horizontal direction, thereby automatically completing the demolding operation of the microneedle patch product.

INDUSTRIAL APPLICABILITY

A microneedle patch base layer lamination and separation device and a control method therefor of the present disclosure integrate a lamination operation and a separation operation. When the lamination operation or the separation operation is performed, a rotation control mechanism controls a rotary table to rotate around a horizontal direction, and at the same time, a movement control mechanism controls a movable seat or a carrier to move in the horizontal direction, which may effectively avoid a problem of defective products caused by the fact that an elastic pressing head and an elastic vacuum suction cup drag an adhesive layer and a support plate to deform in a rotation direction due to the friction between the elastic pressing head and the adhesive layer, and between the elastic vacuum suction cup and the support plate. The degree of automation is high, the operation is stable and reliable, the yield rate is high, the production efficiency is high, and the production cost is low.

According to a microneedle patch base layer lamination device and a control method therefor of the present disclosure, a lamination surface of the elastic pressing head is pressed against a product to be laminated by means of transition from point contact or line contact to surface contact in an elastically deformable manner, thereby avoiding the generation of bubbles in a laminated product and improving the production yield rate. The degree of automation is high, the operation is stable and reliable, the yield rate is high, the production efficiency is high, and the production cost is low.

A microneedle patch demolding and separation device and a control method therefor of the present disclosure control a microneedle patch to be smoothly demolded from a mold at an angle relative to the horizontal direction by lifting, which reduces the action force and resistance borne by the microneedle patch in the demolding process, and can effectively avoid the damage and breakage of a microneedle due to deformation of the microneedle patch in the demolding process, thereby improving the yield rate, and the degree of automation is high, and the operation is stable and reliable, thereby improving the production efficiency and reducing the production cost.

The above embodiment is some embodiments of the present disclosure and is not intended to limit the scope of implementation of the present disclosure. Any equivalent changes or modifications made within the structures, features and principles of the patent scope of the present disclosure shall fall within the scope of the present disclosure.

What is claimed is:

1. A microneedle patch base layer lamination and separation device, comprising a rack, a movement control mechanism, a movable seat, and a lamination and separation apparatus, wherein the lamination and separation apparatus is arranged on the movable seat, a carrier is supported on the rack, and the movement control mechanism is arranged on the rack and is configured to control the movable seat and/or the carrier to move in a vertical direction and a horizontal direction respectively, wherein, the lamination and separation apparatus comprises a rotation control mechanism, a rotary table, an elastic pressing head, and an elastic vacuum suction cup, wherein the rotary table is able to be located above the carrier in the vertical direction, and the rotation control mechanism is configured to control the rotary table to rotate in the horizontal direction; and the elastic pressing head and the elastic vacuum suction cup are respectively arranged on a peripheral wall of the rotary table, and an abutting surface, away from the rotary table, of the elastic vacuum suction cup protrudes out of a lamination surface, away from the rotary table, of the elastic pressing head in a radial direction of the rotary table.

2. The microneedle patch base layer lamination and separation device according to claim 1, wherein,
  the lamination surface is arranged as a quadratic surface, and the lamination surface is bent away from the carrier;
  or, the lamination surface is arranged as a horizontally extended plane, and the lamination surface is tangent to the peripheral wall of the rotary table.

3. The microneedle patch base layer lamination and separation device according to claim 2, wherein,
  the lamination and separation apparatus further comprises at least one mounting base, wherein each of the at least one mounting base is arranged on the rotary table, a peripheral wall of the each of the at least one mounting base extends along the peripheral wall of the rotary table, and the peripheral wall of the each of the at least one mounting base is provided with the elastic pressing head and the elastic vacuum suction cup.

4. The microneedle patch base layer lamination and separation device according to claim 3, wherein,
  the peripheral wall of the each of the at least one mounting base is provided with a plurality of elastic pressing heads and a plurality of elastic vacuum suction cups;
  the plurality of elastic pressing heads are arranged in a circumferential direction of the rotary table and/or an axial direction of the rotary table, and the plurality of elastic vacuum suction cups are arranged in the circumferential direction of the rotary table and/or the axial direction of the rotary table;
  and/or, abutting surfaces of the plurality of elastic vacuum suction cups are located on a same plane;
  and/or, the plurality of elastic pressing heads and the plurality of elastic vacuum suction cups are staggered in a circumferential direction of the rotary table, and/or, the plurality of elastic pressing heads and the plurality of elastic vacuum suction cups are staggered in an axial direction of the rotary table.

5. The microneedle patch base layer lamination and separation device according to claim 3, wherein,
  the elastic pressing head comprises a mounting part, a connecting part, and a lamination part which are connected in sequence, wherein the lamination surface is located on the lamination part, the peripheral wall of the each of the at least one mounting base is provided with an accommodating groove, and the mounting part is embedded in the accommodating groove;
  and/or, the elastic pressing head comprises a mounting part, a connecting part, and a lamination part which are connected in sequence, wherein the lamination surface is located on the lamination part, the mounting part and the connecting part are made from Polydimethylsiloxane (PDMS), a curing agent, and a silica sol in a weight ratio of (12-15):1:(0.5-3), and the lamination part is made from the PDMS, the curing agent, and the silica sol in a weight ratio of (12-15):1:(0-0.5).

6. The microneedle patch base layer lamination and separation device according to claim 1, wherein,
  a product to be laminated is placed on the carrier, and the product to be laminated comprises a microneedle patch, an adhesive layer, and a support plate, wherein the support plate is located between the adhesive layer and a base layer of the microneedle patch, a microneedle array protrudes out of a side, away from the support plate, of the base layer, the support plate is provided with an accommodating hole corresponding to the microneedle array in a penetrating mode, the lamination surface is able to be pressed against a position of the adhesive layer corresponding to the accommodating hole, and the abutting surface is able to be pressed against the support plate; and
  a diameter of the peripheral wall of the rotary table is D, a length of the support plate in a rotation direction of the rotary table is L, and D=(4-5)L.

7. A control method for a microneedle patch base layer lamination and separation device, wherein the microneedle patch base layer lamination and separation device is the microneedle patch base layer lamination and separation device according to claim 1, and the control method comprises a lamination step and a separation step;
  the lamination step comprises:
  controlling, by the movement control mechanism, the movable seat and/or the carrier to move in the vertical direction and the horizontal direction respectively, so that the rotary table is located above a product to be laminated on the carrier in the vertical direction; controlling, by the movement control mechanism, the movable seat and/or the carrier to move in the vertical direction, so that a lamination surface of an elastic pressing head can be pressed against an adhesive layer of the product to be laminated; and
  controlling, by the rotation control mechanism, the rotary table to rotate in the horizontal direction, and at the same time, controlling, by the movement control mechanism, the movable seat or the carrier to move in the horizontal direction, so that the lamination surface is pressed against the adhesive layer for lamination to form a laminated product; and
  the separation step comprises:
  controlling, by the movement control mechanism, the movable seat and/or the carrier to move in the vertical direction and the horizontal direction respectively, so that the rotary table is located above the laminated product of the carrier in the vertical direction; controlling, by the movement control mechanism, the movable seat and/or the carrier to move in the vertical direction, so that an abutting surface of the elastic vacuum suction cup can be pressed against a support plate of the laminated product; and controlling, by the rotation control mechanism, the rotary table to rotate in the horizontal direction, and at the same time, controlling, by the movement control mechanism, the movable seat or the carrier to move in the horizontal direction, and enabling the elastic vacuum suction cup to start vacuum adsorption, so that the elastic vacuum suction cup adsorbs the support plate to perform a separation operation.

8. The control method for the microneedle patch base layer lamination and separation device according to claim 7, wherein,
  one support plate is provided with a plurality of accommodating holes in a penetrating manner, and after the adhesive layer corresponding to one accommodating hole and the base layer of the product to be laminated complete the lamination step, in the rotation direction of the rotary table, the elastic vacuum suction cup at a front end close to the laminated product completing the lamination step starts vacuum adsorption to perform the separation operation, and at the same time, an elastic pressing head at a rear end close to the laminated product completing the lamination step performs a lamination operation on the adhesive layer corresponding to the next accommodating hole.

9. A microneedle patch base layer lamination device, comprising a rack, a movement control mechanism, a movable seat, and a lamination apparatus, wherein the lamination apparatus is arranged on the movable seat, a carrier is supported on the rack, and the movement control mechanism is arranged on the rack and is configured to control the movable seat and/or the carrier to move in a vertical direction and a horizontal direction respectively, wherein, the lamination apparatus comprises a pressure maintaining control mechanism and an elastic pressing head, wherein the elastic pressing head is able to be located above the carrier in the vertical direction, and the pressure maintaining control mechanism is used to control the elastic pressing head to move in the vertical direction;

a lamination surface, close to the carrier, of the elastic pressing head in the vertical direction is arranged as a quadratic surface, and the lamination surface is bent away from the carrier;

or, a lamination surface, close to the carrier, of the elastic pressing head in the vertical direction is inclined relative to the horizontal direction.

10. The microneedle patch base layer lamination device according to claim 9, wherein, a product to be laminated is placed on the carrier, and the product to be laminated comprises a microneedle patch, an adhesive layer, and a support plate, wherein the support plate is located between the adhesive layer and a base layer of the microneedle patch, a microneedle array protrudes out of a side, away from the support plate, of the base layer, and the support plate is provided with an accommodating hole corresponding to the microneedle array in a penetrating mode; and the lamination surface is able to be pressed against a position, corresponding to the accommodating hole, of the adhesive layer, and a projection area of the lamination surface in the horizontal direction is greater than or equal to an adhesion area between the base layer and the adhesive layer.

11. The microneedle patch base layer lamination device according to claim 9, wherein, the lamination surface, close to the carrier, of the elastic pressing head in the vertical direction is inclined relative to the horizontal direction, and an inclination angle between the lamination surface and the horizontal direction is between 1° and 13°.

12. The microneedle patch base layer lamination device according to claim 9, wherein, a contact point when the lamination surface is just pressed against the adhesive layer is a contact point A, a maximum arc contact point after the lamination surface is completely laminated with the adhesive layer is a contact point B, an angle between a connecting line between the contact point A and the contact point B and the horizontal direction is θ, and 26°≤θ≤42°.

13. The microneedle patch base layer lamination device according to claim 9, wherein, the elastic pressing head is made from a combination of Polydimethylsiloxane (PDMS), a curing agent, and a silica sol, and a weight ratio of the PDMS to the curing agent to the silica sol is (12-15): 1:(0-3).

14. The microneedle patch base layer lamination device according to claim 13, wherein, the elastic pressing head comprises a mounting part, a connecting part, and a lamination part which are connected in sequence, wherein the lamination surface is located on the lamination part, and the mounting part and the connecting part are made from the PDMS, the curing agent, and the silica sol in a weight ratio of (12-15): 1:(0.5-3);

and/or, the lamination part is made from the PDMS, the curing agent, and the silica sol in a weight ratio of (12-15): 1:(0-0.5).

15. A control method for a microneedle patch base layer lamination device, wherein the microneedle patch base layer lamination device is the microneedle patch base layer lamination device according to claim 9, and the control method comprises:

controlling, by the movement control mechanism, the movable seat and/or the carrier to move in the horizontal direction, so that the elastic pressing head is located above a product to be laminated on the carrier in the vertical direction;

controlling, by the movement control mechanism, the movable seat and/or the carrier to move in the vertical direction, so that a lamination surface of the elastic pressing head is pressed against an adhesive layer of the product to be laminated; and controlling, by the pressure maintaining control mechanism, the elastic pressing head to move downward in the vertical direction, so that the lamination surface is laminated with the adhesive layer to perform a pressure maintaining operation.

16. A microneedle patch demolding and separation device, comprising a rack, a movement control mechanism, a movable seat, and a demolding and separation apparatus, wherein the demolding and separation apparatus is arranged on the movable seat, a carrier is supported on the rack, and the movement control mechanism is arranged on the rack and is configured to control the movable seat and/or the carrier to move in a vertical direction and a horizontal direction respectively, wherein, the demolding and separation apparatus is able to be located above the carrier in the vertical direction, and the demolding and separation apparatus comprises a clamping part and a separation part, wherein the separation part is movably supported on the movable seat in the vertical direction, and the separation part protrudes out of the clamping part toward the carrier in the vertical direction; and the separation part is configured to force a stripping end of a microneedle patch on the carrier to be demolded, and the clamping part is configured to clamp the stripping end of the microneedle patch.

17. The microneedle patch demolding and separation device according to claim 16, wherein, the separation part is a hook shovel, a hook-off end of the hook shovel is configured to force the stripping end of the microneedle patch to be demolded, and a hook-off surface, connected to the hook-off end, of the hook shovel is configured to support the stripping end of the microneedle patch, and the hook-off surface of the hook shovel extends in an arc shape in the vertical direction, or, the hook-off surface of the hook shovel is inclined relative to the horizontal direction;

or, the separation part is a vacuum suction cup, and the vacuum suction cup is able to absorb the stripping end of the microneedle patch to force the stripping end of the microneedle patch to be demolded.

18. The microneedle patch demolding and separation device according to claim 16, wherein, the clamping part comprises a first clamping jaw, a second clamping jaw, and a clamping jaw control mechanism, wherein the clamping jaw control mechanism may control the first clamping jaw and the second clamping jaw to move toward or away from each other in the horizontal direction; and the demolding and separation apparatus further comprises a clamping control mechanism, wherein the clamping control mechanism is arranged on the movable seat and is used to control the clamping part to move in the vertical direction.

19. The microneedle patch demolding and separation device according to claim 17, wherein, when the separation part is the hook shovel, the clamping part comprises a sliding shovel, a pressing block, and a pressing control mechanism, wherein the sliding shovel is located on a side of the hook shovel in the horizontal direction, the pressing block is located above the sliding shovel in the vertical direction, the pressing control mechanism is configured to control the pressing block to move toward or away from the sliding shovel, the pressing block is able to be pressed against a support surface of the sliding shovel, and the support surface of the sliding shovel is configured to support the stripping end of the microneedle patch; and the support surface of the sliding shovel is inclined relative to the horizontal direction, and a moving direction of the pressing block is perpendicular to the support surface of the sliding shovel.

20. A control method for a microneedle patch demolding and separation device, wherein the microneedle patch demolding and separation device is the microneedle patch demolding and separation device according to claim 16, and the control method comprises:

controlling, by the movement control mechanism, the movable seat and/or the carrier to move in the vertical direction and the horizontal direction respectively, so that the demolding and separation apparatus is located above a mold placed on the carrier in the vertical direction, and the microneedle patch is formed in the mold;

controlling, by the movement control mechanism, the movable seat and/or the carrier to move in the vertical direction, so that the separation part is pressed against the mold or the microneedle patch;

controlling, by the movement control mechanism, the movable seat and/or the carrier to move in the horizontal direction or the vertical direction, so that the separation part forces the stripping end of the microneedle patch to be demolded from the mold;

controlling the clamping part to clamp the stripping end of the microneedle patch; and controlling, by the movement control mechanism, the movable seat and/or the carrier to move in the vertical direction and the horizontal direction, so that the microneedle patch is demolded from the mold at an angle relative to the horizontal direction.

21. The control method for the microneedle patch demolding and separation device according to claim 20, wherein, in a process of demolding the microneedle patch from the mold at an angle relative to the horizontal direction, an inclination angle between the microneedle patch and the horizontal direction is between 43° and 68°.

* * * * *